(12) United States Patent
Henry et al.

(10) Patent No.: US 8,377,711 B2
(45) Date of Patent: Feb. 19, 2013

(54) STROBOSCOPIC LIBERATION AND METHODS OF USE

(75) Inventors: Kent D. Henry, Laramie, WY (US); John Stanley Lovell, Golden, CO (US)

(73) Assignee: ADA Technologies, Inc., Littleton, CO (US)

( * ) Notice: Subject to any disclaimer, the term of this patent is extended or adjusted under 35 U.S.C. 154(b) by 1543 days.

(21) Appl. No.: 11/278,656

(22) Filed: Apr. 4, 2006

(65) Prior Publication Data

US 2006/0219937 A1     Oct. 5, 2006

Related U.S. Application Data

(60) Provisional application No. 60/668,264, filed on Apr. 4, 2005.

(51) Int. Cl.
*G01N 21/76* (2006.01)
(52) U.S. Cl. ............ 436/172; 436/171; 436/177; 356/36
(58) Field of Classification Search ........................ None
See application file for complete search history.

(56) References Cited

U.S. PATENT DOCUMENTS

| | | | |
|---|---|---|---|
| 3,463,591 | A | 8/1969 | Franken et al. |
| 3,680,959 | A | 8/1972 | Schuch et al. |
| 3,748,905 | A | 7/1973 | Fletcher et al. |
| 3,853,503 | A | 12/1974 | Folmer, Jr. |
| 4,040,411 | A | 8/1977 | Rust |
| 4,580,440 | A | 4/1986 | Reid et al. |
| 4,718,268 | A | 1/1988 | Reid et al. |
| 4,754,655 | A | 7/1988 | Parker et al. |
| 4,819,477 | A | 4/1989 | Fisher et al. |
| 4,820,920 | A | 4/1989 | Bather |
| 4,867,796 | A | 9/1989 | Asmus et al. |
| 4,982,176 | A | 1/1991 | Schwarz |
| 5,017,780 | A | 5/1991 | Kutscher et al. |
| 5,092,155 | A | 3/1992 | Rounbehler et al. |

(Continued)

FOREIGN PATENT DOCUMENTS

| | | |
|---|---|---|
| EP | 0485425 | 5/1992 |
| WO | 9427145 | 11/1994 |

(Continued)

OTHER PUBLICATIONS

Handschh, Martin, et al., Laser-induced molecular desorption and particle ejection fromorganic films, 1999, Applied Surface Science, vol. 137, pp. 125-135.*

(Continued)

*Primary Examiner* — Robert Xu
(74) *Attorney, Agent, or Firm* — Sheridan Ross P.C.

(57) ABSTRACT

The invention is directed to a system and method for detecting substances, such as explosives and/or drugs, using, in part, short bursts of energy light from a relatively low energy strobe. Embodiments include coupling the strobe with a detector for use in a portable hand-held unit, or a unit capable of being carried as a backpack. Embodiments further include placement of one or more stroboscopic desorption units and detectors in luggage conveyors systems, carry-on X-ray machines, and check-in counter locations. Embodiments further comprise the use of a strobe or another energy source to assist in maintaining the integrity of a SERS substrate surface operatively associated with the detector system, wherein the SERS substrate may be positioned in hand wand spaced apart from at least a portion of the detector. In another embodiment, the Raman excitation source may be located directly in the hand wand of a portable stroboscopic detection system.

50 Claims, 14 Drawing Sheets

U.S. PATENT DOCUMENTS

| | | | |
|---|---|---|---|
| 5,092,157 | A | 3/1992 | Achter et al. |
| 5,092,218 | A | 3/1992 | Fine et al. |
| 5,092,220 | A | 3/1992 | Rounbehler |
| 5,112,127 | A | 5/1992 | Carrabba et al. |
| 5,122,127 | A | 6/1992 | Stanley |
| 5,138,889 | A | 8/1992 | Conrad |
| 5,147,611 | A | 9/1992 | Stout et al. |
| 5,149,972 | A | 9/1992 | Fay et al. |
| 5,278,418 | A | 1/1994 | Broadhurst |
| 5,476,794 | A | 12/1995 | O'Brien et al. |
| 5,580,733 | A | 12/1996 | Levis et al. |
| 5,585,575 | A | 12/1996 | Corrigan et al. |
| 5,600,700 | A | 2/1997 | Krug et al. |
| 5,663,561 | A | 9/1997 | Franzen et al. |
| 5,693,152 | A | 12/1997 | Carron |
| 5,751,897 | A | 5/1998 | Van Alstyne |
| 5,782,253 | A | 7/1998 | Cates et al. |
| 5,842,995 | A | 12/1998 | Mahadevan-Jansen et al. |
| 5,859,375 | A | 1/1999 | Danylewych-May et al. |
| 5,862,273 | A | 1/1999 | Pelletier |
| 5,904,900 | A | 5/1999 | Bleuse et al. |
| 5,942,699 | A | 8/1999 | Ornath et al. |
| 5,955,729 | A | 9/1999 | Nelson et al. |
| 5,965,884 | A | 10/1999 | Laiko et al. |
| 5,972,638 | A | 10/1999 | Burlage et al. |
| 6,018,389 | A | 1/2000 | Kyle et al. |
| 6,085,601 | A | 7/2000 | Linker et al. |
| 6,127,935 | A | 10/2000 | Davidson et al. |
| 6,191,406 | B1 | 2/2001 | Nelson et al. |
| 6,353,476 | B1 | 3/2002 | Allen et al. |
| 6,446,514 | B1 | 9/2002 | Danylewych-May et al. |
| 6,477,907 | B1 | 11/2002 | Chambers et al. |
| 6,558,626 | B1 | 5/2003 | Aker et al. |
| 6,558,956 | B1 | 5/2003 | Carron et al. |
| 6,614,523 | B1 | 9/2003 | Boss et al. |
| 6,621,574 | B1 | 9/2003 | Forney et al. |
| 6,692,694 | B1 | 2/2004 | Curry et al. |
| 6,723,564 | B2 | 4/2004 | Hillenkamp |
| 6,730,923 | B1 | 5/2004 | May et al. |
| 6,734,423 | B2 | 5/2004 | Bryden |
| 6,735,368 | B2 | 5/2004 | Parker et al. |
| 6,753,396 | B2 | 6/2004 | Ulbricht et al. |
| 6,775,448 | B2 | 8/2004 | Zoorob |
| 6,788,863 | B2 | 9/2004 | Parker et al. |
| 6,797,242 | B2 | 9/2004 | Neumann et al. |
| 6,797,944 | B2 * | 9/2004 | Nguyen et al. ............... 250/286 |
| 6,828,795 | B2 | 12/2004 | Krasnobaev et al. |
| 6,838,663 | B2 | 1/2005 | Coon et al. |
| 6,856,737 | B1 | 2/2005 | Parker et al. |
| 6,861,646 | B2 | 3/2005 | Motchkine et al. |
| 6,870,155 | B2 | 3/2005 | Krasnobaev et al. |
| 6,888,128 | B2 | 5/2005 | Krasnobaev et al. |
| 6,895,804 | B2 | 5/2005 | Lovell et al. |
| 6,897,951 | B2 | 5/2005 | Womble et al. |
| 6,947,132 | B1 | 9/2005 | Boss et al. |
| 6,959,127 | B2 | 10/2005 | Zoorob |
| 6,967,717 | B1 | 11/2005 | Boss et al. |
| 7,016,586 | B2 | 3/2006 | Zoorob et al. |
| 7,027,701 | B2 | 4/2006 | Parker et al. |
| 7,084,397 | B2 | 8/2006 | Hirano et al. |
| 7,116,878 | B2 | 10/2006 | Zoorob et al. |
| 7,162,132 | B2 | 1/2007 | Parker et al. |
| 7,244,288 | B2 | 7/2007 | Belyakov et al. |
| 7,248,770 | B2 | 7/2007 | Parker et al. |
| 7,574,930 | B2 | 8/2009 | Bunker |
| 7,576,320 | B2 | 8/2009 | Bunker et al. |
| 2003/0039299 | A1 | 2/2003 | Horovitz et al. |
| 2003/0133105 | A1 | 7/2003 | Gorelik et al. |
| 2003/0155504 | A1 | 8/2003 | Motchkine et al. |
| 2003/0230152 | A1 | 12/2003 | McGill et al. |
| 2004/0157342 | A1 | 8/2004 | Lovell et al. |
| 2005/0007119 | A1 | 1/2005 | Belyakov et al. |
| 2005/0047702 | A1 | 3/2005 | Parker et al. |
| 2005/0079626 | A1 * | 4/2005 | Kunz ............... 436/164 |
| 2005/0235739 | A1 | 10/2005 | Lovell et al. |
| 2005/0248758 | A1 | 11/2005 | Carron et al. |
| 2006/0062540 | A1 | 3/2006 | Zoorob et al. |
| 2006/0119853 | A1 | 6/2006 | Baumberg et al. |
| 2006/0228251 | A1 | 10/2006 | Schneberger et al. |
| 2006/0256340 | A1 | 11/2006 | Hansen et al. |
| 2007/0015288 | A1 | 1/2007 | Hulteen et al. |
| 2007/0215725 | A1 | 9/2007 | Bunker |
| 2008/0290810 | A1 | 11/2008 | Kiernan et al. |

FOREIGN PATENT DOCUMENTS

| | | |
|---|---|---|
| WO | WO 99/01750 | 1/1999 |

OTHER PUBLICATIONS

International Search Report for International (PCT) Patent Application No. PCT/US2006/012212, mailed Sep. 27, 2007.

Written Opinon for International (PCT) Patent Application No. PCT/US2006/012212, mailed Sep. 27, 2007.

International Preliminary Report on Patentability for International (PCT) Patent Application No. PCT/US2006/012212, mailed Nov. 1, 2007.

Fryer et al., "Dependence of the Glass Transition Temperature of Polymer Films on Interfacial Energy and Thickness," 2001, Macromolecules, vol. 37, No. 16, pp. 5627-5634.

"2,4-Dinitrotoluene Material Safety Data Sheet," Sep. 1997, Toxic Air Contaminant Identification Series, pp. 437-439.

Lewis, J., "Recommendation to List 2,4,6-Trinitrotoluene (TNT) as a Potential Pollutant," Apr. 2001, pp. 1-8.

PCT—Notification of Transmittal of the International Search Report and the PCT International Search Report dated Jun. 22, 2004.

Paul Tompkins et al.; "Icebreaker: An Exploration of the Lunar South Pole," copyright 1999 by the Space Studies Institute, 11 pages.

V.A. Morosov et al.; "2Π spectrometer: A new apparatus for the investigation of ion surface interaction," Rev. Sci. Instrum. 67(6) (Jun. 1996), pp. 2163-2170.

Yvan Simard et al.; "New technology for the detection of micronekton: multivariate acoustics, sampling and data analysis strategies," printed Nov. 13, 2003, 24-pages, available at http://pulson.seos.uvic.ca/meeting/scor2000/simard/simard.html.

V. Debur et al.; "Position-sensitive detector for the 6-meter optical telescope," printed Nov. 13, 2003, 6 pages, available at http://arxiv.org/pdf/astro-ph/0310353.

K. Fransson; "The Trigger System of the CELSIUS/WASA Detector," Physica Scripta T99, (2002), pp. 176-182.

M. Mayer et al.; "Performance of CdZnTe Strip Detectors as Submillimeter Resolution Imaging Gamma Radiation Spectrometers," undated, 5 pages.

U.S. Appl. No. 12/020,419, filed Jan. 25, 2008, Henry et al.

Prism (optics), Wikipedia, the free encyclopedia, available at http://en.wikipedia.org/wiki/Prism_%28optics%29, printed Jan. 18, 2008, pp. 4.

Optical instruments—Wikipedia, the free encyclopedia, available at http://en.wikipedia.org/wiki/Optical_instrument, printed Jan. 18, 2008, pp. 2.

Lens (optics)—Wikipedia, the free encyclopedia, available at http://en.wikipedia.org/wiki/Lens_%28optics%29, pp. 15.

Mirror—Wikipedia, the free encyclopedia, available at http://en.wikipedia.org/wiki/Mirror, printed Jan. 18, 2008, pp. 11.

Internet web page for Mesophotonics regarding Klarite, available at http://www.mesophotonics.com/products/klarite.html, cite updated May 4, 2007, pp. 1-2.

Kambhampati, et al., "On Chemical Mechanism of Surface Raman Scattering: Experiment and Theory", Chem. Phy. 1998(108): 5013-5026.

Background for the above-captioned application (previously provided).

"Global Security Solutions" available at http://www.global-security-solutions.com/, printed Sep. 11, 2009.

Kawai et al. "Application Note #18: Raman Spectroscopy for Homeland Defense Applications" by InPhotonics, 2004, pp. 1-4.

Thiesan et al., "Survey of Commercially Available Explosives Detection Technologies and Equipment 2004", Sandia National Laboratories, Document No. 208861, Feb. 2005, 97 pages.

Examination Report for UK Patent Application No. GB0719072.1, mailed Oct. 12, 2009.

* cited by examiner

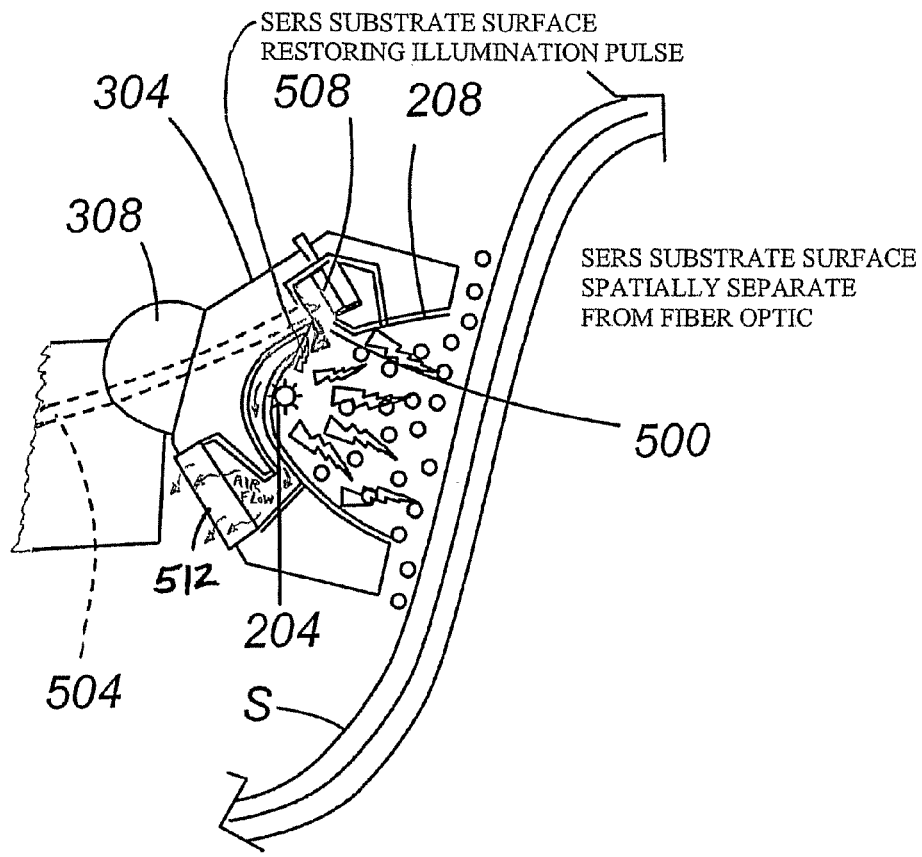
FIG. 5B
FIG. 5C
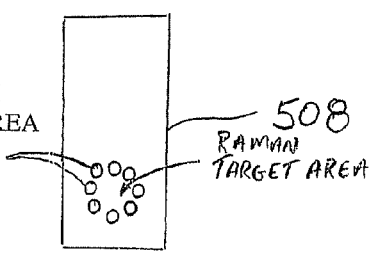
ORIFICES ALLOW FOR AIR FLOW THROUGH
THE SUBSTRATE, RAMAN STIMULATION AREA
AND STROBE ILLUMINATION AREA
FOR SURFACE RESTRORATION
SERS SUBSTRATE SURFACE DETAIL

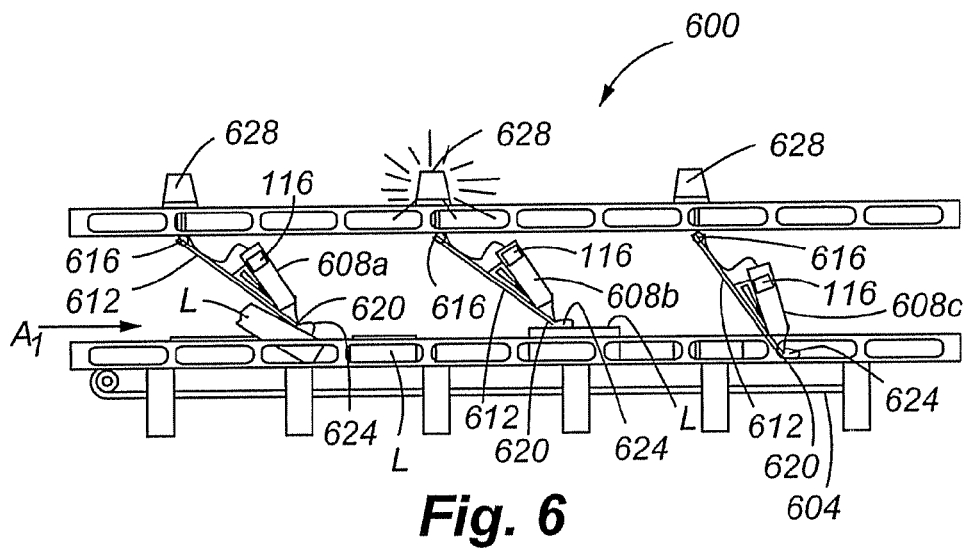
Fig. 6
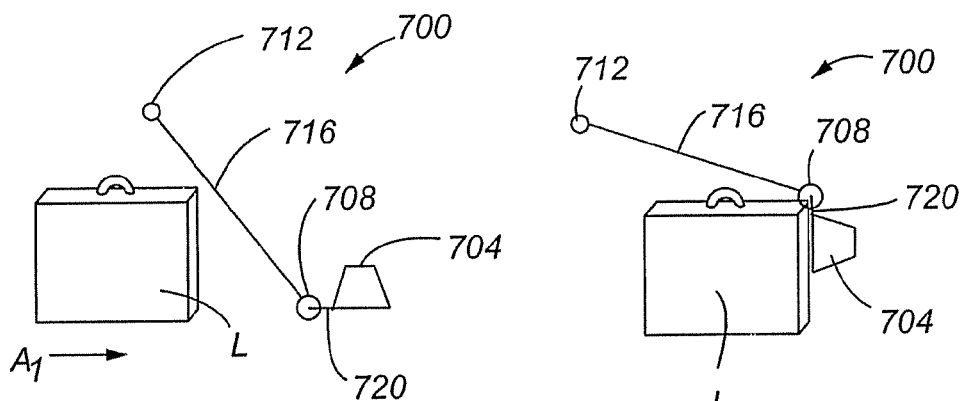
Fig. 7A
Fig. 7B
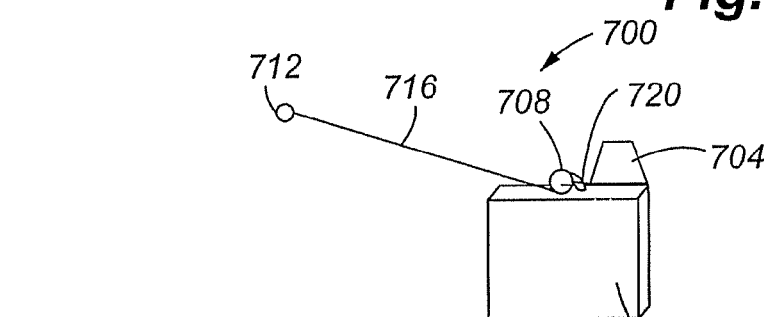
Fig. 7C

*Fig. 9B*
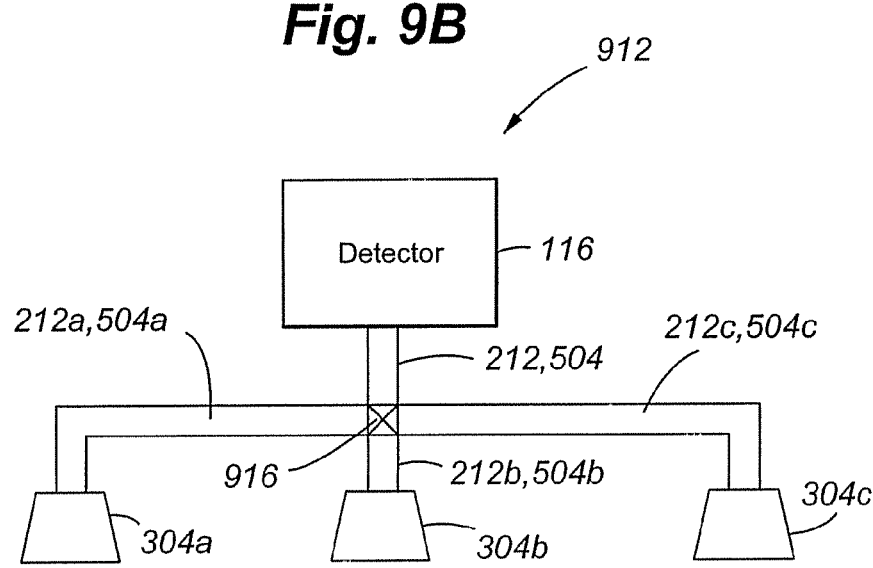
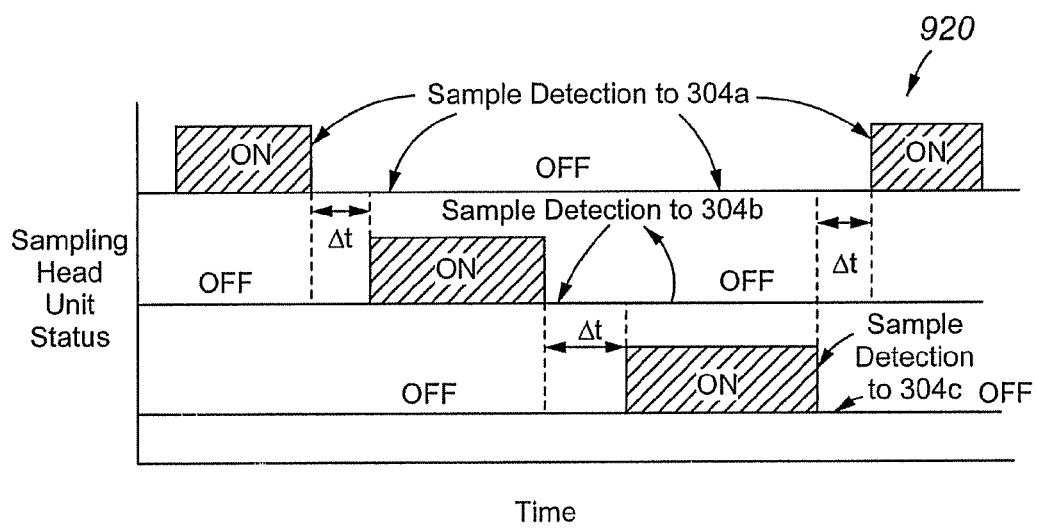
*Fig. 9C*

STROBOSCOPIC LIBERATION AND METHODS OF USE

CROSS-REFERENCE TO RELATED APPLICATIONS

The present application claims the benefit of U.S. Provisional Patent Application No. 60/668,264 filed Apr. 4, 2005 entitled "AUTOMATIC BAGGAGE SCREENING FOR EXPLOSIVES AND NARCOTICS", the content of which is incorporated herein by reference in its entirety. The present application also incorporates by reference the content of U.S. patent application Ser. No. 11/384,172 filed Mar. 17, 2006.

FIELD

The present invention is related to a device and method for liberating a sample from an article using a light pulse and, in at least one embodiment, a relatively low-power strobe light is used for stroboscopic liberation or desorption of compounds and/or particles of interest.

BACKGROUND

Explosives and other controlled substances, such as drugs, have become major societal problems. Increasingly, terrorist acts using explosives are becoming a problem not only for countries in the Middle East but also for Western countries in other parts of the world. Explosives constitute a weapon used by terrorists and insurgents, wherein the explosives may be hidden in a myriad of devices; however, it is typically difficult for a person handling explosives to avoid contamination after coming into contact with an explosive or explosive device because explosives readily adhere to surfaces.

In addition to explosives, drug abuse has been a longstanding problem for Western countries and consumes large amounts of law enforcement resources each year. Canines, metal detectors, and "sniffer" detectors have been used at various locations, such as airports, border crossings, and the like to detect explosive devices and illegal drugs. These measures have had mixed success.

Another measure that has been employed to detect contraband substances has been to collect loose particles from surfaces or skin with a vacuum cleaner or a swipe. The swipe or the particles collected by the vacuum are then heated to release the vaporizable material for analysis. This approach is in routine use at airports throughout the world for screening airline passengers. An example of such a system is the Barringer™ Ion Scan System™; however, this technique has drawbacks. For example, the use of swipes or particle vacuums is an intermittent process, which requires manual intervention between the sampling and analysis. This is a time consuming approach that is inherently slow, although it may optionally be used in conjunction with at least one embodiment of the present invention.

Previously disclosed devices for volatilizing certain substances for detection include a high-energy apparatus disclosed in U.S. Pat. No. 6,895,804. The content of U.S. Pat. No. 6,895,804 is incorporated herein by reference in its entirety. The landmine detection apparatus of the '804 patent applies a relatively high amount of energy to the sample target that is generally intended to be soil. To provide the requisite energy, the radiation source of the '804 patent is powered by a relatively high amount of energy, and therefore, is limiting in its ability to serve as a self-contained backpack unit, handheld device, or other relatively compact portable device. In addition, high-energy strobes are slow to recharge, utilize kilowatts of energy to power, and are heavy as a self-contained unit that includes a power source.

U.S. Pat. No. 6,828,795, incorporated herein by reference, suggests use of an ion mobility spectrometer with a heat source, but energy levels have not been provided. U.S. Patent Application Publication No. 2005/0007119 A1, related to the '795 patent, is also incorporated herein by reference. The '795 patent discloses using an electrostatic precipitator to take out particulates, presumably to keep them out of the ion mobility spectrometer. It is noted here that, in at least one embodiment, the present invention advantageously releases a plume of particulates that is then able to form at least part of the signal.

Typical trace explosive detectors employing vapor and/or particle analyses rely on an interval-based analysis that requires discrete and separate steps for (1) sampling and (2) detection. The combination of these two steps may take anywhere from 15 to 60 seconds, or more. Thus, it would be advantageous to provide an apparatus for sampling multiple target surfaces while the detector is processing the sampled information.

Surface Enhanced Raman Spectroscopy (SERS) can be used for trace detection of chemical contaminants, such as explosives or drugs. SERS employs microscopically roughened, or "activated" metals, normally noble metals, that adsorb the compound of interest. Existing SERS detectors have traditionally been hindered in application due to the length of time that the SERS substrate surface remained available for new sample material to adsorb to the nano-texture of the substrate. Therefore, the SERS substrate requires cleaning or refreshing to continue to function properly. Such cleaning of the substrate surface has been accomplished in prior art by a number of methods.

One such method includes disposing of the used substrate and using a new substrate. As a result, this further requires the effort of recalibration of the signal amplification factor, or otherwise having to fabricate the substrate surface using extreme precision controls so that recalibration is not necessary. Either way, the result is high costs because of instrument down-time for substrate replacement and costs associated with fabrication and procurement of the replacement substrates.

Another way of refreshing the SERS substrate is to heat the substrate to desorb the adsorbed materials. This is slow and requires considerable power to heat and subsequently re-cool the substrate, thus making it unattractive for battery powered equipment.

A further method of cleaning or refreshing the SERS substrate is to increase the ambient air flow across the substrate surface to favor desorption of the adsorbed materials from the substrate due to solid-gas partitioning. However, this process will only restore the surface over time if the air flowing across the surface is clean and does not contain other materials that will in-turn adsorb on the surface. In addition, this method relies on rather slow thermodynamics and the time it takes will cost the system overall power in idle time. In general, this process is slow because the desorption of contaminants with low vapor pressures is particularly time consuming.

Yet another method of cleaning or refreshing the SERS substrate is to remove the substrate and clean the substrate using solvent rinsing, heating, and/or wiping with a clean or solvent soaked swab. Although relatively quick, this costs labor, is prone to human neglect and/or error, and is subject to irreproducibility. Furthermore, contaminates from the cleaning process may also adsorb onto the substrate. Thus, it would be advantageous to provide an improved means for refreshing or cleaning the SERS substrate.

As noted above, present techniques for airport security include sometimes screening baggage for trace explosives by manually swiping the surface of the baggage and analyzing the swipe, such as by using Ion Mobility Spectrometry. Not all bags are tested for trace explosives, with carry-on baggage typically being X-rayed but not always screened for traces of explosives. Thus, there would be an advantage to automatically screening all baggage, whether checked or carry-on, for explosives. In addition, upon arrival at a destination airport, government agencies at the destination airport typically also screen baggage, wherein such screen efforts typically include searches for drugs. Thus, it would be advantageous to be able to automatically screen baggage upon arrival, such as when baggage is unloaded from international flights. Accordingly, among other types of screening uses, such as crime scene analysis, there is clearly a need for automatically screening airline baggage and carry-on items for traces of explosives and drugs.

SUMMARY

In one embodiment, the present invention is directed to a relatively low-energy system and associated methods for detecting substances, such as high boiling point and low vapor pressure materials, using energy radiation imparted by a suitable radiation source, such as a relatively low energy strobe, over a short time period. Examples of substances that are detectable include explosives and other controlled substances, such as drugs, chemical warfare agents and toxic industrial chemicals. "Explosives" refer to a chemical compound, usually containing nitrogen, that detonate or deflagrate as a result of shock or heat. "Drugs" refer to a substance that acts on the central nervous system, e.g., a narcotic, hallucinogen, barbiturate, or psychotropic drug. "Chemical warfare agents" refer to chemical compounds designed kill, injure or incapacitate persons. "Toxic industrial chemicals" refer to chemical compounds used in industry for productive and otherwise safe purposes but which are toxic upon direct exposure.

The sampling of vapor comprises gas-phase molecules that are emitted from a solid or liquid. The concentration of target substances in the air is related to the vapor pressure of the target substance and to other factors such as the amount of time the target substance is present in a location, its affinity to local substrates, its packaging, air circulation in the location, etc. The sampling of particulate matter is also possible and may be facilitated by stroboscopic desorption. Here, microscopic particles of the solid target substance or non-target substance to which the target substance is attached is sampled. For example, explosives material that adheres to surfaces such as by direct contact with the explosive, or indirectly, through contact with someone's hands who has been handling explosives.

The target material can be a variety of possible substances, including a semi-volatile co-contaminant or a high boiling point and/or low vapor pressure material or a derivative thereof. Typically, a high boiling point material has a boiling point of at least about 150° C., more typically of at least about 250° C., and a low vapor pressure material is a material having a vapor pressure of no more than about $2\times10^{-3}$ mm Hg and more typically of no more than about $2\times10^{-4}$ mm Hg under conditions of standard temperature and pressure (STP). The derivative can itself be a high boiling point and/or low vapor pressure material. Typical substances of interest include at least one of an explosive compound, an explosive related compound, a chemical warfare agent, a drug, an industrial compound or toxic industrial compound (TIC), and derivatives thereof. Examples of TNT derivatives include dinitrotoluene, 2-ADNT and 4-ADNT. Such derivatives can be unique markers to the presence of the source substance. Examples of target materials include explosives, such as TNT, nitroglycerine, ammonium nitrate, acetylides of copper and/or silver, mercury fulminate, lead azide, diazodinitrophenol, nitrosoguanidine, lead styphnate, cyclotrimethylenetrinatramine or RDX, pentaerythritol tetranitrate or PETN, triacetone triperoxide or TATP, dynamite, semtex, EGDN, DMNB, H-6, C-4, picric acid, nitrocellulose, and illicit drugs such as cocaine, heroin, opium, marijuana, methamphetamines, LSD, and co-contaminants from the manufacturer or purification of these drugs.

The sample area can be any suitable animate or inanimate surface. The methods provided herein have particular application to the detection of substances for security and drug enforcement operations. Accordingly, the sample area can be a variety of surfaces, including, but not limited to, the skin of a body part, such as a hand, clothing, shoes, documents including travel documents, currency, weapons and weapon components, luggage, bags, mail, packages, envelopes, metal, glass, plastic and painted surfaces, refuse, biological or biological related matter, vehicles, cargo containers, furniture surfaces, flooring, wood and canvas.

In accordance with some embodiments of the present invention, liberation of target substances can be achieved by using extremely short bursts of energy light in the form of stroboscopic desorption. When used in combination with a detector, this liberation technology is termed stroboscopic signal amplification. By using stroboscopic signal amplification, the detection limits of a traditional trace vapor detector may be increased by two or more orders of magnitude over a traditional trace vapor detector that does not use stroboscopic signal amplification. Accordingly, as a result of the mechanism of stroboscopic signal amplification, the vapor mode detection of currently available instrumentation is able to momentarily sample both an enhanced vapor concentration and liberated particles from the surface under study. Thus by employing stroboscopic enhanced trace chemical detection, there is less reason to operate a trace chemical detector in particle mode employing the manual steps employing a swipe, although a swipe could first be performed if desired. For example, a swipe could be obtained from inside a relatively small container, such as a narrow tube, and then the swipe tested, such as by using stroboscopic signal amplification and an associated detector. To work most efficiently with stroboscopic signal amplification, the trace detector should have an optimized vapor inlet that prevents condensation of low vapor pressure compounds and entrapment of particulates before being either directly detected or deposited on the detector's internal preconcentrator.

Advantageously, strobe desorption can liberate explosive- and/or drug-bearing particulates from surfaces for detection. Low-energy strobes provide an attractive radiation source for liberating a sample from an article because they have a low capacity for heating with minimal to negligible heating of the sample substrate. That is, the heating from a low-energy strobe is sufficient to cause some vaporization or physical liberation through plume generation of target constituents on the surface of the article, but less heating of the sample substrate relative to a high-energy strobe. As a result, the low energy strobe of the present invention is suitable for operating on a wide range of articles, wherein the low energy strobe yields acceptably low or negligible heat damage to the subject articles. In addition, low energy strobes are relatively fast to recharge, use watts (versus kilowatts) of energy and light, and are suitable for use in relatively compact configurations, including battery operated backpack and/or handheld sampling devices. Accordingly, as those skilled in the art will appreciate, the present invention has application to a wide variety of uses, including personnel screening, such as at transportation facilities, large public gathering places, political events, and prisoner intake. In addition, as further illustrated herein, embodiments of the present invention have application to screening objects, such as clothing, footwear, baggage, vehicles, containers, packages, mail and documents.

Some embodiments of the present invention are directed at obtaining samples of compounds from a sample surface, such as those articles mentioned directly above. Those skilled in the art will appreciate that high amounts of energy imparted to the sample surface can generate a gas-phase or airborne sample to achieve this goal. Difficulty exists in providing a relatively low power mechanism that does not burn or otherwise appreciably damage the sample surface. However, a minimum value of energy, as described herein, is necessary in order to assist in desorption or liberation of particles or compounds from the sample surface. Accordingly, in at least one embodiment of the invention, a strobe light is provided, wherein a relatively short burst of light is directed to the sample surface, the energy from the light causes some heating of the surface to vaporize some types of compounds (low vapor pressure compounds) and/or generates a relatively small heat shock to the sample surface that creates a plume, thereby lifting particles. However, the heating of the sample surface is not enough to cause damage to surfaces typically encountered on luggage, travel documents, clothing, or even skin. Thus, in accordance with embodiments of the present invention, the stroboscopic source provides a non-pyrolizing apparatus for liberating a material from a sample surface, although the detector mechanism may incorporate a pyrolizing apparatus once the sample is collected. In accordance with embodiments of the present invention, the stroboscopic source may also provide desorption of non-target components, thereby liberating target substances.

In a separate aspect of the invention, deployment of a stroboscopic desorption and associated detection device can be used to automatically screen luggage, packages and/or a variety of articles. In some embodiments of the invention, stroboscopic desorption and detection is conducted during pick-up and or conveyance of the luggage or packages, such as along a conveyor belt that carries the luggage to the intended airplane or other mode of transportation (such as train, ship, or vehicle). Such screening system may be used, as for example, in an the vicinity of an existing X-ray machine, thereby allowing all of the baggage to be screened for explosives or other target substances, with little or no increase in personnel. The invention can also be applied to automatically screen baggage for illicit drugs as it is unloaded from international flights prior to customs.

Thus, in one embodiment of the invention, a system for detecting at least one chemical located on a sample surface is provided, the system comprising a first strobe for imparting an energy to the sample surface, the first strobe providing between about 0.4 to 5 Joules of energy per square centimeter of the sample surface area as measured at the sample surface, wherein the energy liberates the at least one chemical from the sample surface. In addition, the system comprises a detector, a detector mechanism, or a means for detecting the at least one chemical upon liberation by the energy. In accordance with some embodiments of the present invention, at least a portion of the energy is transmitted to the sample surface during an initial discharge peak interval of less than about 100 microseconds. In addition, in accordance with one or more embodiments, the first strobe is powered by at least one battery, such as a 6-volt dc battery. In addition, in accordance with one or more embodiments of the invention, the first strobe is positioned within a reflector, the reflector having a parabolic shape in side profile, the parabolic shape described by an equation $x^2=4py$, wherein p equals at least one half of the diameter of a flash lamp portion of the strobe. In accordance with some embodiments, the means for detecting further comprises means for sampling at least one of an airborne particle and compound associated with the at least one chemical. Furthermore, in one or more embodiments, the means for sampling comprises at least one of a pump and a fan. In some embodiments, the means for detecting comprises a fiber optic. In one or more embodiments, the means for detecting is selected from the group consisting of spectroscopy, thermoredox, chemiluminescence, and spectrometry, and in one or more embodiments, the means for detecting comprises surface enhanced Raman spectroscopy. In accordance with some embodiments of the invention, the system may further comprise a second strobe located proximate the first strobe and directed at the sample surface, and one or more embodiments, the first and second strobes may be operatively associated with a common shroud. In yet other embodiments, the system is operatively associated with a conveyance mechanism for moving the sample surface from a first position to a second position, wherein the first position is not in sampling proximity of the first strobe and wherein second position is in sampling proximity with the first strobe. In addition, in one or more embodiments, the first strobe is interconnected to a hand wand, the hand wand spaced apart from at least a portion of the means for detecting. In other embodiments, the first strobe is interconnected to sampling head, the sampling head operatively associated with at least one of a handle, a hand wand, a check-in counter, an X-ray machine, a conveyor belt, a biasing member, and a hinged arm. In addition, in one or more embodiments, the means for detecting comprises a preconcentrator. For systems comprising a hand wand, embodiments of the present invention may also comprise a proximity sensor that determines if a sample surface is under the strobe head before allowing the strobe to be activated. Such embodiments may comprise radar, a pressure switch and/or an optical sensor. Such a proximity sensor aids in ensuring that the operator is actually sampling a surface.

In some embodiments of the invention, a system for detecting at least one of an explosive, an explosive related compound, a chemical warfare agent, a toxic industrial compound, a drug, and derivatives thereof is provided, the system comprising at least one strobe, wherein the strobe emits a pulse of light to a sample surface comprising the explosive, explosive related compound, chemical warfare agent, toxic industrial compound, drug, and/or derivatives thereof, the pulse of light providing an energy at the sample surface of between about 0.4 to 5 Joules per square centimeter of the sample area. In addition, the system comprises a sampling mechanism operatively associated with the strobe, wherein the sampling mechanism samples the air proximate the sample surface. In addition, the system comprises a detector communicating with the sampling mechanism. The system may further comprise other features as described herein.

In some embodiments of the invention, a luggage trace chemical detection system for detecting at least one of an explosive, an explosive related compound, a chemical warfare agent, a toxic industrial compound, a drug, and derivatives thereof, from a luggage surface is provide, the system comprising at least one strobe, wherein the strobe emits an energy pulse of light to the luggage surface, a sampling mechanism operatively associated with the strobe, wherein the sampling mechanism samples the air proximate the luggage surface, and a detector communicating with the sampling mechanism. In one or more embodiments of the invention, at least a portion of the energy pulse is transmitted to the luggage surface during an initial discharge peak interval of less than about 100 microseconds. In addition, in some embodiments of the invention, the first strobe is interconnected to a sampling head, the sampling head operatively associated with at least one of a handle, a hand wand, a check-in counter, an X-ray machine, a conveyance mechanism, a floor, a sample container, a vehicle, a flap, a conveyor belt, a biasing member, and a hinged arm. In at least some embodiments of the invention, the first strobe is positioned within a reflector, the reflector having a parabolic shape in side profile, the parabolic shape described by an equation $x^2=4py$, wherein p equals at least one half of the diameter of a flash lamp of the strobe. In at least one embodiment of the invention, the system is operatively associated with a conveyance mechanism for moving the sample surface from a first position to a second position, wherein the first position is not in sampling proximity of the first strobe and wherein second position is in sampling proximity with the first strobe. In some embodiments of the invention, the energy pulse of light is between about 0.4 to 5 Joules per square centimeter at the luggage surface. In addition, in accordance with embodiments of the present invention, a proximity sensor is provided that determines if a sample surface is under the strobe head before allowing the strobe to be activated. Such embodiments may comprise radar, a pressure switch and/or an optical sensor. Such proximity sensors aid in ensuring that an object in the vicinity of the sampling head is actually an appropriate sampling surface. In addition, the system may further comprise other features as described herein.

Various embodiments of the present include a variety of advantageous features. In at least one embodiment, an ergonomic hand wand allows the user to access difficult and/or hard to reach sample locations, wherein, in at least one embodiment, the hand wand implements stroboscopic signal amplification in combination with SERS.

In accordance with some embodiments of the present invention, a SERS substrate geometry may be used for optimum compound deposition. In addition, the substrate may be oriented for stroboscopic surface restoration by photon reception directly from a strobe. Furthermore, the substrate is preferably positioned for receiving the sample plume and facilitating adsorption of compounds from the sample plume, wherein, in at least one embodiment, the substrate is situated in a flow path provided by a pump or fan. In one embodiment of the present invention, the SERS substrate is a separate component spatially separated from a fiber optic. The light interacts with the substrate surface oriented toward the outlet of the fiber optic. In an alternative embodiment, the SERS substrate comprises a thin film surface modification of the end of the fiber optic (or an insert over the end of the fiber optic) that allows the light to interact with adsorbed species at the fiber end.

Thus, in at least one embodiment of the invention, surface enhanced Raman scattering is performed on a trace chemical after the trace chemical is liberated from a sample using a strobe. A system for detecting at least one chemical located on a sample surface, the system comprising: (a) a first strobe for imparting an energy to the sample surface, wherein the energy liberates the at least one chemical from the sample surface; (b) a SERS substrate operable to adsorb the at least one chemical liberated from the sample surface; and (c) a detector operable to detect the at least one chemical, the detector in operative communication with the SERS substrate. The first strobe provides between about 0.4 to 5 Joules of energy per square centimeter of the sample surface area as measured at the sample surface. In accordance with embodiments of the present invention, an optical path is provided between the first strobe and the SERS substrate, wherein photons emitted from the first strobe clean at least a portion of the substrate prior to the at least one chemical being adsorbed on to the SERS substrate. The system may further comprise a photon emitter directed to the SERS substrate other than the first strobe, the photon emitter providing at least a pulse of photons for impinging the SERS substrate. The photon emitter may comprise a second strobe. Alternatively, the photon emitter may comprise a laser LED. In accordance with embodiments of the present invention, the strobe and the SERS substrate are co-located within a hand wand. In accordance with at least one embodiment of the invention, the strobe and the SERS substrate are co-located within a sampling head. In accordance with embodiments of the present invention, the system further comprises at least one of a pump and a fan, the at least one pump and a fan for conveying an airborne sample containing the at least one liberated chemical over the SERS substrate. In accordance with embodiments of the present invention, the at least one of a pump and a fan also thermally cools at least one of the strobe and the SERS substrate. In addition, the sampling head may be operatively associated with at least one of a handle, a check-in counter, an X-ray machine, a conveyance mechanism, a floor, a sample container, a vehicle, a flap, a conveyor belt, a biasing member, and a hinged arm. In accordance with embodiments of the present invention, the sampling head comprises a shroud, and in at least one embodiment, the shroud comprises a reflector, wherein the first strobe is positioned within the reflector, the reflector having a parabolic shape in side profile, the parabolic shape described by an equation $x^2=4py$, wherein p equals at least one half of a diameter of a flash lamp portion of the first strobe. In addition, in at least one embodiment of the invention, the system further comprises at least a second strobe located proximate the first strobe and co-directed at the sampling surface. An adjacent plurality of strobes may be operatively associated with a common shroud.

In accordance with some embodiments of the invention, a SERS substrate is used in combination with a Raman excitation source, such as a laser LED, wherein the Raman excitation source may be located spaced apart from the detector, such as between the detector and the sampling head of the apparatus. Thus, in one embodiment of the invention, a system for detecting at least one chemical located on a sample surface is provided, the system comprising: (a) a SERS substrate operable to adsorb the at least one chemical liberated from the sample surface; (b) a Raman excitation source for providing an excitation of the SERS substrate; and (c) a detector operable to detect the at least one chemical, the detector in operative communication with the SERS substrate; wherein the SERS substrate and the Raman excitation source are spaced apart from the detector. In accordance with embodiments of the present invention, a radiation source is provided for imparting an energy to the sample surface, wherein the energy liberates the at least one chemical from the sample surface. In accordance with embodiments of the present invention, the radiation source may comprise at least one strobe. In accordance with embodiments of the present invention, the SERS substrate and the Raman excitation source are both located in a hand wand operably interconnected to the detector. In accordance with embodiments of the present invention, the system further comprises an optical path between the radiation source and the SERS substrate, wherein photons emitted from the radiation source clean at least a portion of the substrate prior to the at least one chemical being adsorbed on to the SERS substrate. In accordance with embodiments of the present invention, the system further comprises a photon emitter other than the radiation source, the photon emitter providing at least a pulse of photons for impinging and cleaning the SERS substrate.

Some embodiments of the present invention are also directed to methods of detecting a chemical. Accordingly, in an embodiment of the present invention, a method for detecting a trace chemical from a sample surface is provided, the method comprising: (a) pulsing a strobe directed at the sample surface, the strobe imparting an energy to the sample surface of between about 0.4 to 5 Joules of energy per square centimeter of the sample surface area as measured at the sample surface, wherein the energy liberates a material from the sample surface; (b) collecting the material in an airborne sample; and (c) detecting the trace chemical from the material. In addition, in at least one embodiment, the material comprises one or more of a particle and a compound in the airborne sample. In another embodiment, the method may further comprise moving the sample surface under the strobe prior to the pulsing step. In addition, in an embodiment of the method, the collecting step comprises the substep of providing at least one of a pump and a fan to pull the material toward at least a portion of a detector before the detecting step. In another embodiment, the method may further comprise activating an alarm after the detecting step. In some embodiments, at least one of the collecting and the detecting steps comprise the substep of transporting the collected sample through a heated conduit to a detector. In an embodiment of the method, at least a portion of the energy is transmitted to the sample surface during an initial discharge peak interval of less than about 100 microseconds. In addition, in one or more embodiments, the trace chemical comprises a high boiling point and/or low vapor pressure, and wherein the trace chemical comprises is at least one of an explosive, an explosive related compound, a chemical warfare agent, a drug, a toxic industrial compound, and derivatives thereof. In one or more embodiments of the invention, the collecting step comprises the substep of conveying the airborne sample to a preconcentrator, and the substep of conveying may further include conveying a plurality of airborne samples to the preconcentrator before the step of detecting.

In yet another embodiment of the invention, a method for detecting a trace chemical from a sample surface is provided, the method comprising: (a) pulsing a strobe directed at the sample surface, wherein the energy liberates the trace chemical from the sample surface; (b) collecting the trace chemical in an airborne sample; (c) causing a surface enhanced Raman scattering of the trace chemical; and (d) detecting the trace chemical. In accordance with embodiments of the invention, the airborne sample comprises one or more of a particle and a compound. In accordance with embodiments of the invention, the method further comprises moving the sample surface under the strobe prior to the pulsing step. In accordance with embodiments of the invention, the collecting step comprises the substep of providing at least one of a pump and a fan to pull the airborne sample a SERS substrate before the detecting step. In accordance with embodiments of the invention, the method further comprises activating an alarm after the detecting step. In accordance with embodiments of the invention, at least one of the collecting and the detecting steps comprises the substep of transporting the collected sample through a heated conduit. In accordance with embodiments of the invention, at least a portion of the energy is transmitted to the sample surface during an initial discharge peak interval of less than about 100 microseconds. In accordance with embodiments of the invention, the trace chemical comprises a high boiling point and/or low vapor pressure, and wherein the trace chemical comprises is at least one of an explosive, an explosive related compound, a chemical warfare agent, a drug, a toxic industrial compound, and derivatives thereof. In accordance with embodiments of the invention, the collecting step comprises the substep of conveying the airborne sample to a preconcentrator. In accordance with embodiments of the invention, the substep of conveying further includes conveying a plurality of airborne samples to the preconcentrator before the step of detecting. In accordance with embodiments of the invention, the strobe imparts an energy to the sample surface of between about 0.4 to 5 Joules of energy per square centimeter of the sample surface area as measured at the sample surface. In accordance with embodiments of the invention, the method further comprises placing a hand wand in sampling proximity of the sample surface prior to the pulsing step. In accordance with embodiments of the invention, the hand wand includes the strobe and a SERS substrate for adsorbing the trace chemical and for conducting at least a portion of the surface enhanced Raman scattering. In accordance with embodiments of the invention, the method further comprises cleaning the substrate using photons. In accordance with embodiments of the invention, the photons of the cleaning step are emitted from the strobe. In accordance with embodiments of the invention, the photons of the cleaning step are emitted from a laser. In accordance with embodiments of the invention, the photons are emitted from a laser LED located in the hand wand.

Various embodiments of the present invention are set forth in the attached figures and in the detailed description of the invention as provided herein and as embodied by the claims. It should be understood, however, that this Summary may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 5B is a side elevation view of a hand wand sampling device used with the apparatus shown in FIG. 4A, wherein the sampling head is shown in cut-away, and wherein a SERS substrate surface is separate from the Raman fiber;

FIG. 5C is a detail view of the SERS substrate shown in FIG. 5B;

FIGS. 6-9A are views of various automated stroboscopic sampling systems in accordance with embodiments of the present invention;

FIG. 9B is a schematic of a portion of an embodiment of a detection apparatus with a plurality of sample heads and a means for conveying sample or sample information to an associated detector;

FIG. 9C is a graph illustrating an "on/off" timing configuration for using multiple sampling heads for an embodiment of the present invention;

DETAILED DESCRIPTION

Figure 1:
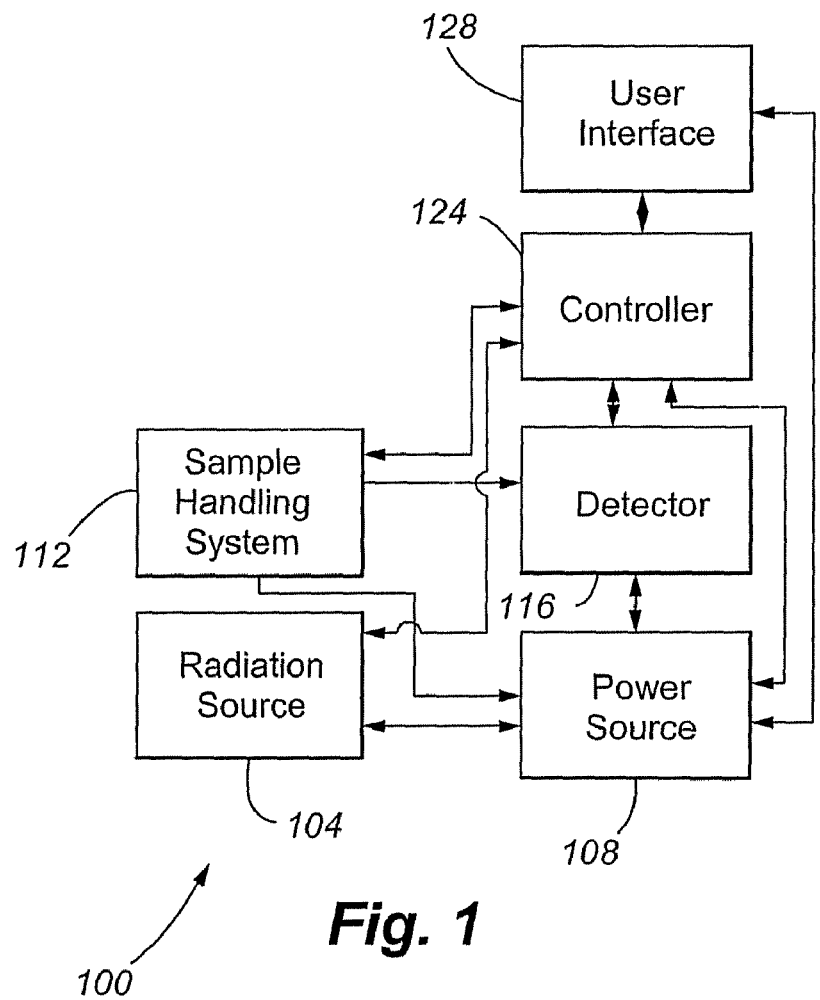
FIG. 1 is block diagram depicting components of a system in accordance with embodiments of the present invention.

In accordance with embodiments of the invention, a radiation source is provided for liberation or desorption of material from a sample. One or more embodiments of the present invention may be used for explosives detection, chemical warfare agent detection, toxic industrial chemical detection, and detection of narcotics or drugs, and has additional application to a variety of other uses, including analysis of medical room cleanliness, foods, chemicals, coatings, etc. The present invention preferably utilizes a strobe for providing the radiation source, thereby yielding a stroboscopic signal amplification device that can be used with a variety of different types of detectors, as discussed in more detail below. In general, the strobe provides a non-damaging discharge of energy over a relatively very short period of time, such as on the order of several hundreds of microseconds for the total light pulse. This results in a discharge from the strobe that takes relatively very little power, but releases a substantial amount of energy. The light energy from the strobe has a relatively broad bandwidth, from visible to infrared wavelengths, and is directed toward the target surface, where the sample surface may comprise, such as by way of example and not limitation, a surface of a piece of luggage, package, skin surface, fabric surface, currency or document.

Stroboscopic desorption is believed to provide signal amplification via two mechanisms. First, energy from the strobe heats the surface to increase the vapor pressure of high boiling point (low vapor pressure) compounds, thereby placing vapors of the compounds into the airspace above the sample surface. Second, mechanical shock generated by the strobe creates a plume of micron and sub-micron particles from the surface. The shock comes in two separate parts: (a) rapid expansion of heated air at the flash lamp interface with the atmosphere; and (b) rapid absorption of energy at the illuminated medium causing the ejection of particulates from the target surface. In general, particle liberation is due to the shock associated with the energy absorption at the sample surface and not from the heating of the air in the vicinity of the flash tube. Indeed, the present invention can function even if a piece of glass is placed between the strobe and the target surface. Therefore, the mechanism for liberating the sample from the target surface is a function of the coupling of the light generated by the strobe and the absorption of light by the target surface.

One advantage of the present invention is that it does not rely on the use of ultrasonic vibrations, air bursts, and/or continuous infrared or continuous visible spectrum light illumination (which is very power intensive) to liberate the sample from the target surface, although one or more of these features, such as air bursts, could be used with the present invention. Because the power requirements of the present invention are relatively low, the strobe of the present invention may be powered on direct current batteries, such as AA batteries, D cell batteries, lithium or nickel metal hydrides, or other comparable battery packs. This directly contrasts with stroboscopic desorption systems of the prior art that use relatively large amounts of power.

A first possible embodiment of a detection system of the present invention is depicted in FIG. 1. The detection system 100 includes a radiation source 104, a power source 108, a sample handling system 112, a detector 116, a controller 124, and a user interface 128. The detection system 100 illuminates a sample area with radiation emitted by the radiation source 104, transports a sample collected at or near the sample area using the sample handling system 112 to the detector 116, and measures the concentration of or otherwise detects the presence of one or more target substances using the detector 116. The sample contains liberated and/or volatilized materials, including the target material(s) to be detected, if present.

Referring again to FIG. 1, the radiation source 104 can be any suitable radiation emitter capable of emitting broadband radiation or radiation in one or more desired wavelength bands. Although any range of radiation wavelengths that will be rapidly absorbed by the target and the underlying surface may be used, such as infrared and visible, the source 104 typically outputs energy in the wavelength range of from about 300 nm to about 700 nm in the visible wavelengths and 700 nm to 2 microns in the infrared region of the electromagnetic spectrum. Preferred radiation emitters include flash lamps, also known as strobes. In accordance with embodiments of the present invention, and as discussed in more detail below, the amount of energy provided at the sample substrate surface is considered, as opposed to just the cumulative or total energy output of the strobe, although this value is of interest in order to control the power source requirements for a portable, self-contained trace chemical detection system that includes both the stroboscopic signal amplification components and the detector.

The controller 124 is typically a microprocessor with volatile and/or nonvolatile memory. The controller 124 receives and responds to feedback from various sensors, if used, such as temperature sensors, voltage sensors, current sensors, and the like, as well as commands from a user. In addition, the controller issues appropriate control signals to system components. The controller 124 may further process measurement signals received from the detector 116 and interface with the user interface 128 to provide the measurements in a selected format to a user. For example, the controller 124 can apply calibration equations and scaling factors to convert signal magnitude into a measurement value and/or compare the signal magnitude and/or measurement value to predetermined thresholds to determine whether a target or non-target substance is present. The controller can also issue warning signals in the event of system malfunction.

The user interface 128 can be any suitable interface depending on the application. The interface 128 can provide audio and/or video feedback to the user. For example, the interface 128 can be an audio and/or visual and/or vibratory alarm when a target material is detected, a display identifying substances detected and their concentrations, a warning light that is illuminated when a target material is detected, and any combination of the foregoing. The user interface can also include user controls, such as buttons, toggles, switches, keys, and the like to provide user commands to the controller 124.

Figure 2:
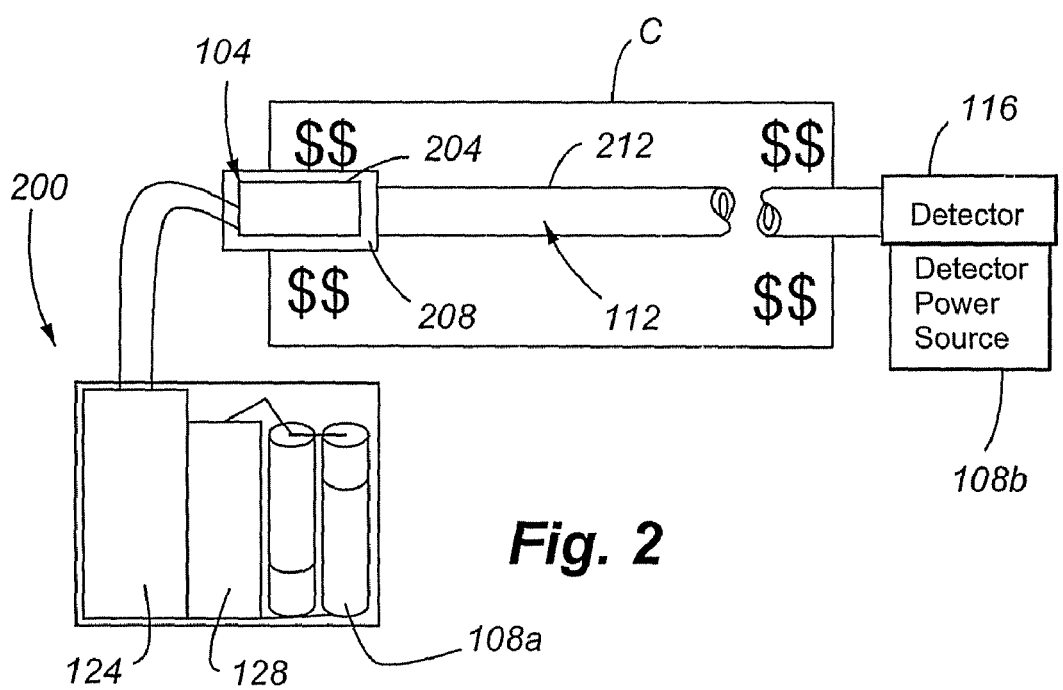
FIG. 2 is a top view of a stroboscopic signal amplification device used to obtain a sample from a note of currency.

Referring now to FIG. 2, an embodiment of the present invention is illustrated, wherein the device is used to obtain a sample from a document, and more particularly, from a note of currency C. The detection system 200 of FIG. 2 includes a radiation source 104 comprising a strobe light 204. In accordance with at least one embodiment of the present invention, and by way of example and not limitation, for effective low vapor pressure and particle desorption, a desired minimum energy at the sample surface is about 0.4 J/cm$^2$. Such energy per unit surface area value provides significant increase in the concentration of airborne compounds and/or particles from the sample, as compared to using a detector without strobe signal amplification.

Figure 13A:
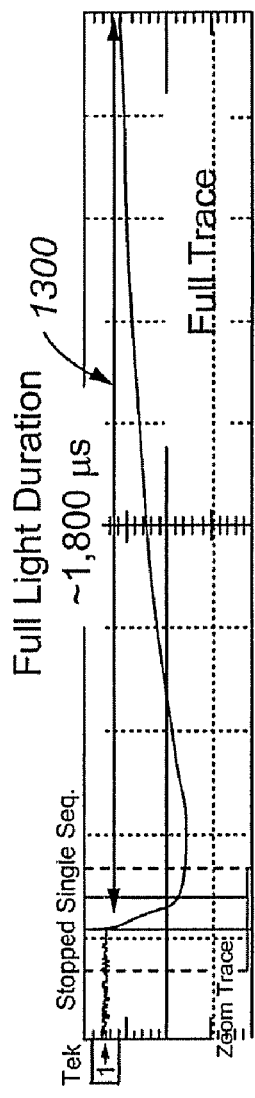
FIGS. 13a and 13b are full trace and zoom trace graphs, respectively, of illumination versus time for an example flash event in accordance with at least one embodiment of the present invention.
Figure 13B:
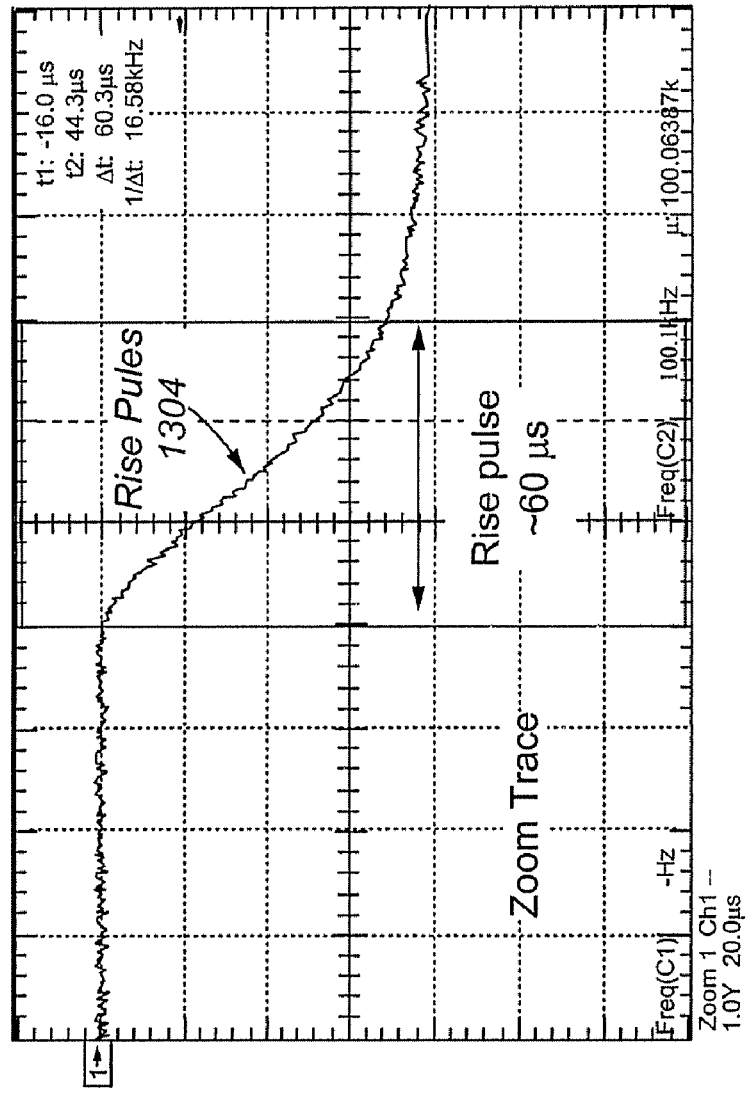

In terms of energy per area per time to peak discharge, that is, the initial time it takes for the strobe to go from zero to peak illumination flux, the value for the present invention is about 6 mJ/cm$^2$/µs, calculated as 0.4 J/cm$^2$ divided by 60 µs, where, in one embodiment, the peak illumination flux time is about 60 µs. However, embodiments of the present invention may operate with a time to peak discharge as low as about 5 µs, thereby yielding about 80 mJ/cm$^2$/µs (calculated as 0.4 J/cm$^2$ divided by 5 µs) for the energy per area per time to peak discharge. As defined herein, the "time to peak discharge" or "rise pulse" means the duration of moving from zero illumination to maximum illumination where the sample surface and substrate are absorbing radiant energy. FIG. 13a illustrates a full trace for illumination detection of an experiment performed in accordance with at least one embodiment of the present invention. For the full trace shown in FIG. 13a, the full light duration 1300 extended about 1,800 µs. Other embodiments of the present invention may have a shorter full light duration or a full light duration of up to about 3,000 µs, wherein the value of the full light duration depends on the amount of heating desired at the surface in combination with the intensity of the heating of the surface. FIG. 13b illustrates an enlarged view or zoom trace of the initial portion of the illumination example shown in FIG. 13a. For the zoom trace of FIG. 13b, the front-end duration of the discharge or rise pulse 1304 extends about 60 µs. It is noted that time to peak discharge or corresponding rise pulse for the strobe of the '804 patent is about 600 µs, which is significantly longer than the relatively low-energy strobe device of the present invention.

Of course other values are operable for the present invention other than those just described, and such other values are considered within the scope of the present invention, with the foregoing values provided for purposes of enablement and not to be limiting upon the scope of the claims. Thus, depending upon the type of sample surface being screened, at least 0.4 J/cm$^2$ of energy should be applied at the sample surface; however, higher levels are desirable, so long as the sample surface is not damaged. Accordingly, embodiments of the present invention should use an energy level at the sample surface that does not carbonize or burn the surface, and such levels are anticipated to be less than about 5 J/cm$^2$. Therefore, embodiments of the present invention should use an energy level at the sample surface preferably of between about 0.4 to 5.0 J/cm$^2$, and more preferably, between about 0.4 to 3.0 J/cm$^2$, and more preferably yet, between about 0.4 to 1.5 J/cm$^2$, wherein the lower levels just noted are more appropriate for portable devices that rely on a battery source, and wherein higher energy level devices just described can be used where an AC power source is nearby, provided the energy source is adjusted sufficiently low so as to cause little or no damage to the sample surface. Furthermore, in accordance with embodiments of the present invention, the time to peak discharge or rise pulse is preferably less than about 300 µs, and more preferably, less than about 200 µs, and more preferably yet, less than about 100 µs, and still more preferably yet, about 60 µs, with a low value of about 5 µs. The above noted values for energy level at the sample surface and time to peak discharge properly combine to provide sufficient heating of the sample surface with sufficient shock to the sample surface, while also not damaging the sample surface.

A reflector 208 may be used to direct the light generated from the strobe 204 to the sample surface. In accordance with at least one embodiment of the invention, the strobe 204 is positioned within a reflector 208, wherein the reflector 208 has a parabolic shape in side profile, and wherein the parabolic shape can be described by an equation $x^2=4py$, wherein p is preferably equal to one half the diameter of the flash lamp plus a gap to allow air circulation between the flash lamp and the reflector surface. The reflector preferably comprises a highly reflective material that is also suitable for contact with a variety of compounds, and in one or more embodiments, comprises aluminum or an aluminum alloy. In addition, if properly configured with a sampling port, the reflector 208 may optionally act as an airborne sample containment structure or shroud to temporarily isolate the sample area below the strobe and above the sample surface for collection and transport to one or more elements associated with the detector 116. Alternatively, the reflector 208 may be set at a standoff distance from the surface to be sampled, with a sample collection means situated proximate the sample surface for collection of liberated airborne compounds and particles.

The strobe 204 is preferably in electrical communication with a controller 124, wherein the strobe 204 and controller 124 are powered by a power source. For the detection system 200 of FIG. 2, a first power source 108a is interconnected to the controller 124, user interface 128, and strobe 204. In accordance with at least one embodiment of the invention, the power source 108a comprises one or more batteries, such a two AA batteries.

The detection system 200 further comprises a sample handling system 112 that comprises a tube 212 that leads to detector 116, wherein the sample handling system 112 and/or detector 116 include a means, such as a pump or fan, for generating a gaseous and particulate flow through the tube 212 in the vicinity of the strobe 204 and reflector 208. In accordance with at least one embodiment of the present invention, the tube 212 may include sample conditioning functionality, such a means for heating the airborne sample (for example, heat tape, hot air, etc.) within the tube 212 to prevent condensation of the sampled vapor from being deposited on the inner wall of the tube 212 during transport form the location of the sampled area to the detector 116. Thus, in accordance with embodiments of the invention, the present invention may include tubing, piping, and/or other conveyance structures for transporting an airborne sample comprising at least a portion of any volatilized high boiling point and/or low vapor pressure materials (or other sample particles, compounds, chemicals, elements, etc.) liberated from the sample surface through an inlet and through a heated conduit to the detector 116, wherein an internal surface of the heated conduit is maintained at a temperature sufficient to inhibit absorption and/or condensation of the high boiling point and/or low vapor pressure material on the internal surface of the tubing, piping and/or conveyance structures.

In accordance with the embodiment of the invention shown in FIG. 2, the detector 116 includes a second power source 108b. For the embodiment shown in FIG. 2, the controller 124 may be in communication with the detector 116, such as by a wireless communication device or by wiring.

Figure 3:
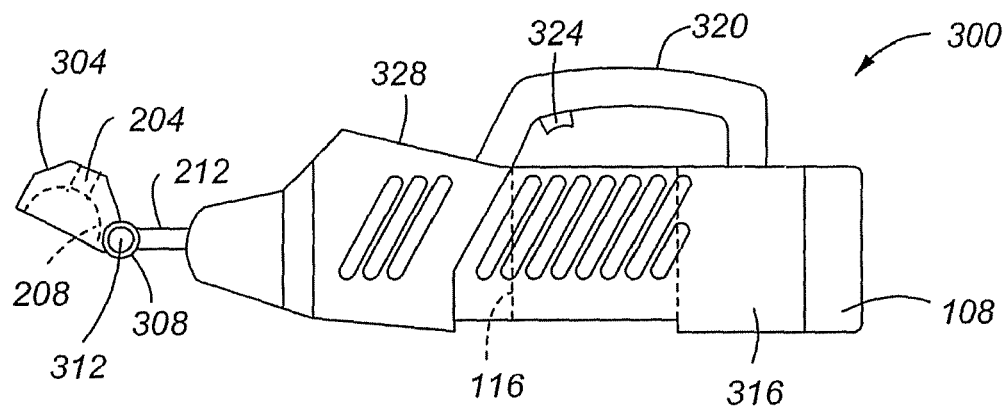
FIG. 3 is a side elevation view of a self-contained hand-held stroboscopic sampling apparatus in accordance with at least one embodiment of the present invention.

Referring now to FIG. 3, a portable detection system in the form of a handheld stroboscopic liberation or desorption apparatus 300 is shown. In accordance with at least one embodiment of the invention, the handheld stroboscopic desorption apparatus 300 includes a strobe 204 mounted within a sampling head 304 having a reflector 208, wherein the sampling head 304 can pivot about a swivel mechanism 308. The swivel mechanism 308 may include a spring 312 or other device for biasing the sampling head 304 in a downward direction so that the sampling head 304 is generally maintained in close proximity to the sample surface. Although not shown, a vented skirt may be provided around the sampling head 405 to help maintain the plume dispersion and to act as a soft point of contact when in operation. In addition, one or more proximity sensors may optionally be used to prevent the strobe 204 from activating unless there is a surface under the strobe for analyzing.

The handheld stroboscopic desorption apparatus 300 preferably includes a tube 212 leading to a detector 116 that is located within a housing 316. In accordance with at least one embodiment of the invention, the housing 316 includes a handle 320 for manipulating the unit by the user. The handle 316 also preferably includes a trigger 324 for activating the unit. For portable usage, the handheld stroboscopic desorption apparatus 300 includes a power source 108 in the form of a battery pack for powering all of the unit's associated components, including the strobe 204 and the detector 116. Of course, the handheld stroboscopic desorption apparatus 300 may be interconnected to another separate power source, such as an AC outlet where the device is used in a location where electrical power is provided. The handheld stroboscopic desorption apparatus 300 also preferably includes a screen 328 as part of the user interface 128, wherein information is displayed to the user, as for example, the status of the strobe, the status of the detector and detector results.

In a separate aspect of the invention, the strobe 204 may flash a plurality of times during a single sampling event. For example, upon squeezing the trigger 324 once, the strobe 204 may emit two or more pulses or flashes of light spaced apart in time. The detector 116 may then report a single result for the sample generated and collected from the plurality of flashes. This method of providing a plurality of flashes for a single sampling event may be used for all of the various stroboscopic desorption devices of the present invention.

In use, the operator of the handheld stroboscopic desorption apparatus 300 manipulates the sampling head 304 into a position in relatively close proximity to a surface of interest, but not necessarily in contact with the surface. The user then activates the unit by pressing the trigger 324, thereby activating the strobe 204 and engaging the detector 116 to collect the sample and analyze the sample for substances of interest, such as explosive compounds and/or drugs.

Figure 4A:
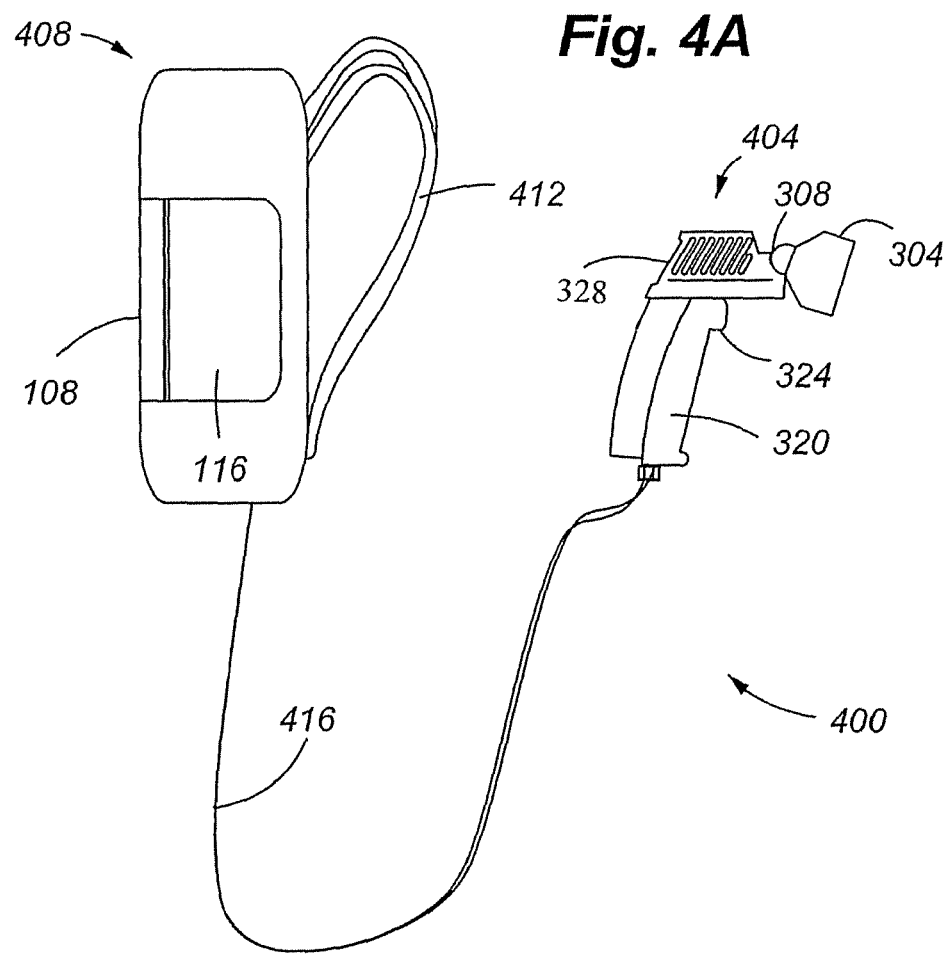
FIG. 4A is a side elevation view of a portable stroboscopic sampling apparatus in accordance with at least one embodiment of the present invention.

Referring now to FIG. 4A, and in accordance with at least one embodiment of the present invention, a portable detection system in the form of a wearable device or backpack stroboscopic desorption apparatus 400 is illustrated that comprises a handheld sampling wand 404 interconnected to a backpack portion 408 having straps 412. The backpack portion 408 preferably includes a detector 116 and a power source 108. A signal cable or umbilical cord 416 interconnects the handheld sampling wand 404 to the backpack portion 408. Thus, in accordance with embodiments of the present invention, a signal cable 416 is used to facilitate optical, power, and/or other communication between a hand wand 404 and a detector 116, power source 108, and other system components. The signal cable 416 preferably incorporates features that prevent or minimize undesired signal loss, for example, due to excessive bending of the one or more fiber optic responsible for excitation and detection for systems using SERS.

The backpack stroboscopic desorption apparatus 400 with backpack portion 408 and wand 404 is particularly suited for field efforts and/or security operations, such as at security checkpoints. For example, the backpack stroboscopic desorption apparatus 400 may be used by a security person checking vehicles for explosives at a vehicle checkpoint. Here, the security person is able to move around the vehicle and test a plurality of locations on the vehicle for traces of explosives or drugs. The backpack stroboscopic desorption apparatus 400 easily facilitates this use because the wand 404 can be used to check the exterior door handles and/or other exterior surfaces, such as the exterior opening panels of a compartment or trunk. Furthermore, the backpack stroboscopic desorption apparatus 400 can be used to also check at least portions of the vehicle's interior space by using the wand 404 to check upholstery, the steering wheel, glove box, aim rests and other interior surfaces and/or spaces as may be present.

Figure 4B:
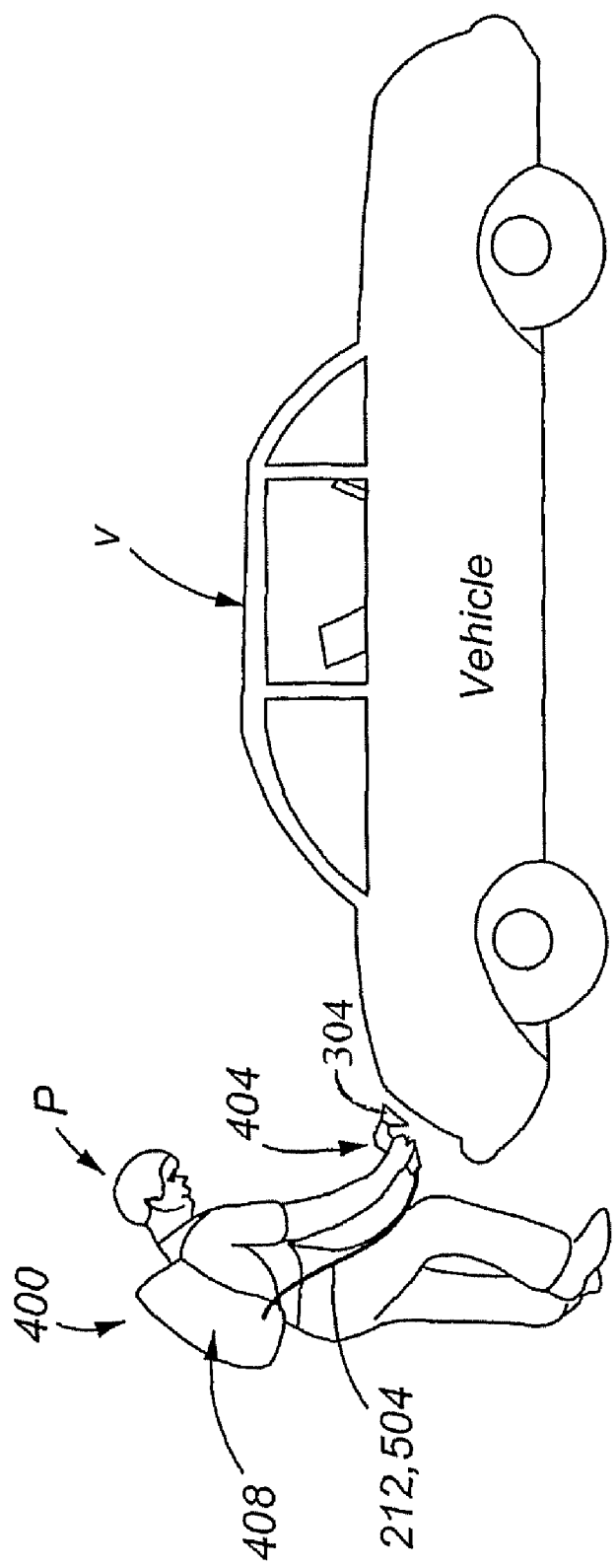
FIG. 4B is a side elevation view the apparatus of FIG. 4A in use by person scanning a surface of a vehicle.

Referring now to FIG. 4B, and in accordance with an embodiment of the invention, a person P is shown using backpack stroboscopic desorption apparatus 400 to scan a trunk area of a vehicle V. In use, the person is preferably wearing backpack 408 and holding the wand 404 substantially adjacent a surface of the vehicle V.

Figure 5A:
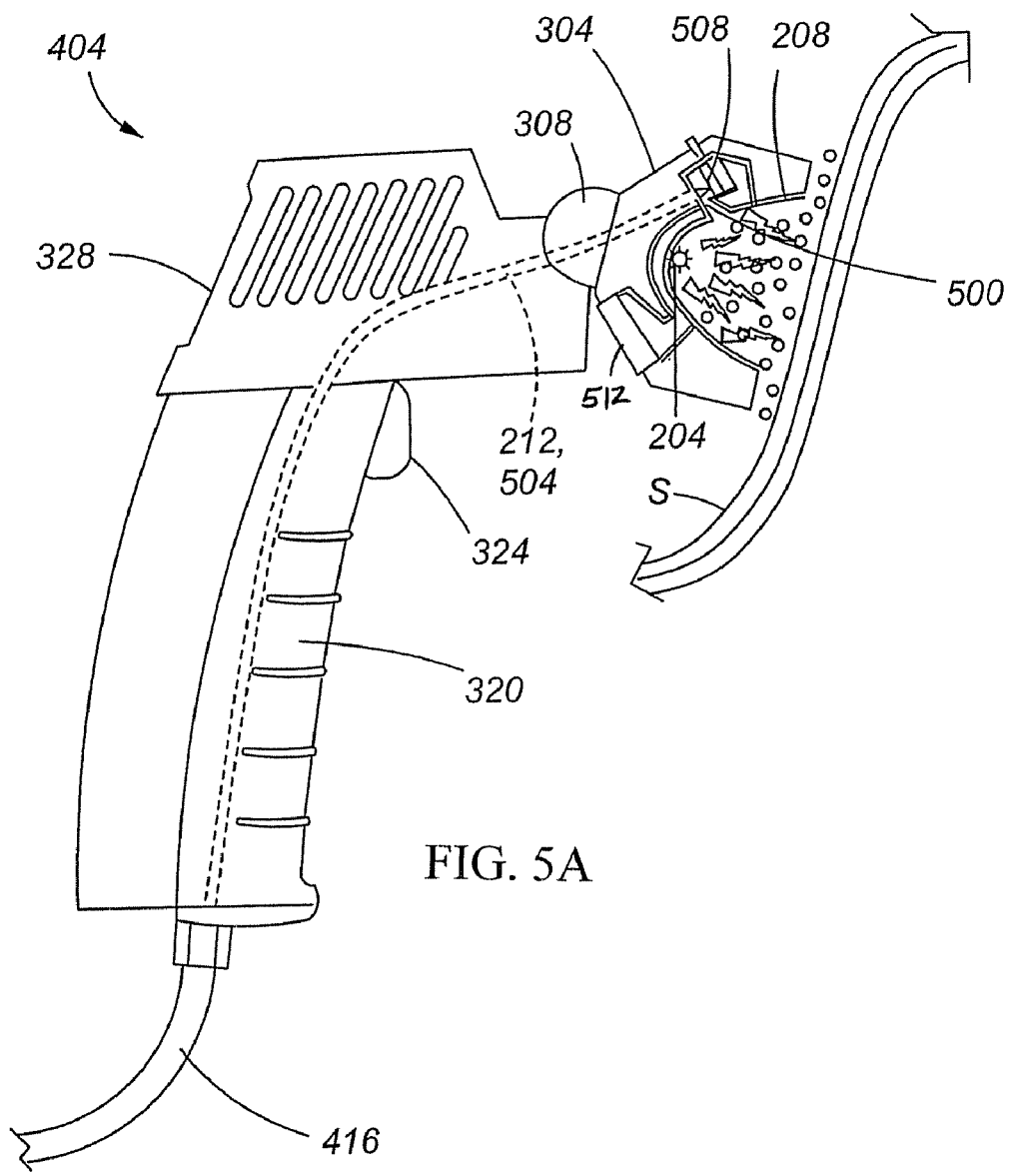
FIG. 5A is a side elevation view of a hand wand sampling device used with the apparatus shown in FIG. 4A, wherein the sampling head is shown in cut-away.

As best seen in FIG. 5A, the umbilical cord 416 preferably includes fiber optic 504 and/or sampling tubing 212, as well as wiring for electrically connecting the wand 404 to the other components of the stroboscopic desorption apparatus 404 positioned in the backpack portion, such as the power source 108.

Referring now to FIG. 5A, an enlarged view of the handheld sampling wand 404 is illustrated. In accordance with at least one embodiment of the present invention, the wand 404 includes a strobe 204 residing within a sampling head 304 that includes a parabolic shaped reflector 208. The wand 404 preferably includes a grip handle 320 with a trigger 324 for activating the unit to emit a strobe flash and collect a sample for analysis. Although not shown, the unit may also include a means for detecting the proximity of a sample surface that will prevent the strobe from activation unless a sample surface is present.

In accordance with at least one embodiment of the invention, an upper portion of the wand 404 preferably includes a screen 328 or other means for displaying information to the user. FIG. 5A also illustrates that the sampling head 304 is preferably positioned in relatively close proximity to the sample surface S. In at least one embodiment, a port 500 is provided in the reflector 208 of the sampling head for accessing the airborne sample after the flash from the strobe 204. A pump or fan 512 may be provided to provide positive or negative pressure to pull the airborne sample toward the port 500. In one embodiment, the airborne sample is transmitted through tube 212 of the umbilical cord 416 to the backpack portion 408 for analysis by the detector 116. Alternatively, as discussed in more detail below, the airborne sample may be optically interrogated at the sampling head itself on a collection substrate 508, with data then transmitted to the detector 116.

In use, the operator of the backpack stroboscopic desorption apparatus 400 grasps the handheld sampling wand 404 and positions the sampling head 304 of the wand 404 adjacent the sampling surface S. The user then activates the strobe 204 by squeezing the trigger 324. The strobe 204 then flashes and the detector 116 of the backpack stroboscopic desorption apparatus 400 collects an airborne sample through a port 500 in the reflector 208 of the sampling head 304 for optical analysis at a collection surface 508 by the detector 116 located in the backpack portion 408.

There are at least four fundamental detector technologies that are amenable to implementation with stroboscopic signal amplification and that are in a product state that is robust and field portable, and still other detector systems are appropriate for more stationary detector locations. With regard to portable detectors, these detector technologies are Surface Enhanced Raman Spectroscopy (SERS), thermo-redox, chemiluminescence and ion mobility spectrometry (IMS). The three former systems spatially separate the sample activation and collection from the bulk of the detector and electronic subsystem. Accordingly, these systems are particularly adapted for use in a portable detection configuration, such backpack stroboscopic desorption apparatus 400. However, they may also be used in more stationary configurations that utilize stroboscopic desorption.

In accordance with embodiments of the present invention, the portable stroboscopic desorption system 400, when used with a SERS based detector, includes one or more of the following advantageous features: a lightweight, agile handheld stroboscopic signal amplification head preferably comprising an integrated SERS substrate including vapor/particulate handling; explosive and/or drug species identification; power, electronics and optical detection components contained in backpack or other unit reducing handheld weight and bulk; status and alarm indicators on the hand wand; wireless communications to a remote server, monitoring station, and/or a vehicle inspection security system; and simple maintenance of the hand wand SERS and stroboscopic signal amplification components.

In SERS, the low vapor pressure compounds and particulates liberated using stroboscopic signal amplification are collected on a substrate surface located at the end of a fiber optic in close vicinity of the target surface. Referring again to FIG. 5A, a fiber optic 504 may be provided between the sampling head 304 and the detector 116. In accordance with at least one embodiment of the present invention, the fiber optic 504 facilitates spectroscopic analysis, such as ultraviolet, ultraviolet-visual light, infrared, Raman, luminescence, and fluorescence techniques. In at least one embodiment, the fiber optic 504 extends to the vicinity of port 500, wherein the airborne sample is pulled using a pump or fan 512 to the a SERS substrate surface 508 for optical scanning by the fiber optic 504. The detector 116 and its associated electronics may be up to several meters away, making the instrument ideal for an ergonomic backpack field instrument, such as system 400. In use, this makes for a very light and agile hand wand 404 for surface probing, including probing of irregular surfaces and surface that are difficult to access. Thus, one embodiment of the present invention comprises placing a strobe 204 for stroboscopic signal amplification in the vicinity of the sample surface S and/or fiber optic 504 associated with a SERS system. SERS has the advantage of being able to identify explosives via spectroscopic analyses and is able to match chemical signatures to internal spectral libraries for conclusive identification without requiring a gas phase separation, such as gas chromatography or ion mobility spectrometry. InPhotonics of Norwood, Mass. currently manufactures SERS systems, and it is believed that such a system is readily adaptable for use with a stroboscopic liberation or desorption device of the present invention.

In accordance with embodiments of the present invention, a fan 512 and/or insulation or other means may be used to keep the SERS substrate 508 thermally isolated and relatively cool. For example, when positioned in a hand wand 404, the SERS substrate 508 may be thermally isolated or cooled within the hand wand. In addition, and in accordance with embodiments of the present invention, an automated air flow algorithm may be used to direct a sample versus "clean air" across the SERS substrate surface 508. In accordance with embodiments of the present invention, airflow from a single pump or fan 512 may be used to direct sample across a SERS substrate 508 while simultaneously cooling the stroboscopic lamp head 204 and the SERS substrate 508. Alternatively, a plurality of fans or pumps may be used.

In accordance with at least one embodiment of the present invention, the hand wand 404 includes active detector features. More particularly, the hand wand 404 may include an excitation source, such as a laser diode for generating the excitation laser light to be directed to the SERS substrate 508.

As noted earlier, typical trace explosive detectors employing vapor/particle analyses rely on an interval-based analysis that requires discrete and separate steps for (1) sampling and (2) detection. The combination of these two steps may take anywhere from 15 to 60 seconds, or more. Of these detectors, only optical-based detectors are capable of performing these two steps in less than 15 seconds, thereby allowing the detector to monitor for the presence of trace explosives in near real-time, with typical delays of less than a few seconds. In accordance with embodiments of the present invention, a stroboscopic desorption apparatus using SERS allows for the collection of data real-time. Although a stroboscopic desorption apparatus using SERS requires additional processing time to compare the spectral results to the internal spectral libraries to identify the presence of an explosive chemical signature, this processing time is dependent upon processing capabilities, and thus, can be reduced with faster processors, but moreover, a stroboscopic desorption apparatus using SERS does not slow the operator performance with respect to sampling multiple target surfaces in rapid succession. Thus, in accordance with embodiments of the present invention, the stroboscopic desorption system, such as the backpack stroboscopic desorption apparatus 400, may be used to sample a plurality of target surfaces while processing continues uninterrupted for the one or more target surfaces that have been sampled. In accordance with embodiments of the present invention, a trace explosive detector used in combination stroboscopic signal amplification, such as a stroboscopic desorption apparatus using SERS, may use a vapor inlet that prevents condensation of low vapor pressure compounds and entrapment of particulates before being deposited on the detector's internal preconcentrator.

In accordance with embodiments of the present invention, an accessory to the hand wand 404 is provided, and/or a mechanism is provided for extending or detachably removing the sampling head 304 containing the strobe 204 and fiber optic 504, wherein the fiber optic 504 is positionable directly on liquids to perform Raman spectroscopy of the liquids. Thus, the present invention is both adaptable and versatile, allowing for surface and liquid analyses. Such embodiments preferably utilize logic to recognize the mode of operation and log the mode of operation with the data, and also report such information as desired.

In accordance with embodiments of the present invention, an accessory may be provided for allowing thermal transfer, such as conductive heat transfer from the thermal reservoir, to facilitate screening of surfaces that do not typically work with a strobe, such as unpainted, shiny metallic surfaces or mirrors.

In a separate aspect of the invention, a stroboscopic desorption apparatus includes a means for cleaning, maintaining, restoring, refreshing, and/or improving the operating integrity of a sensor surface. As noted above, one embodiment of the present invention includes a stroboscopic desorption apparatus using SERS, and at least one embodiment of the present invention includes using an energy source to refresh the SERS substrate. Referring now to FIG. 5B, the sampling head 304 of a wand 404 is shown, wherein the SERS substrate 508 is spatially separated from the fiber optic 504 that comprises the Raman fiber. In accordance with embodiments of the present invention, FIG. 5C, illustrates a detail view of the SERS substrate, wherein orifices are provided for allowing air flow through the substrate 508, Raman stimulation area, and strobe illumination area for refreshing and/or restoring the surface of the SERS substrate 508.

At least one embodiment of the invention uses a "slip-stream" of strobe photons to refresh a SERS substrate surface 508. The surface 508 is restored within a few microseconds, or at least within less than 200 ms, and prior to the arrival of the subsequent vapor and/or particle plume from the target surface S. This restorative feature significantly enhances the operation life and sensitivity of the SERS substrate 508. In addition, the sensitivity of the detector 116 is maintained due to an enhanced signal to noise ratio, and further, due to an overall reduction in accumulated background materials adsorbed on the substrate surface 508. In one embodiment, the hand wand 404 incorporates optics for directing and/or focusing at least a portion of the strobe photons on to the substrate active area. Such surface cleaning or restoration of the SERS substrate 508 overcomes a major challenge in the need to fabricate bulk replacement substrates with identical nanostructure to provide consistent Raman signal amplification. Since the SERS substrate surface 508 is non-destructively refreshed using stroboscopic pulses from the strobe 204, the utility and life of a single substrate 508 is improved, thereby advantageously limiting system down-time for maintenance, as well as improved usability, and lower operational costs of the SERS system.

Figure 5D:
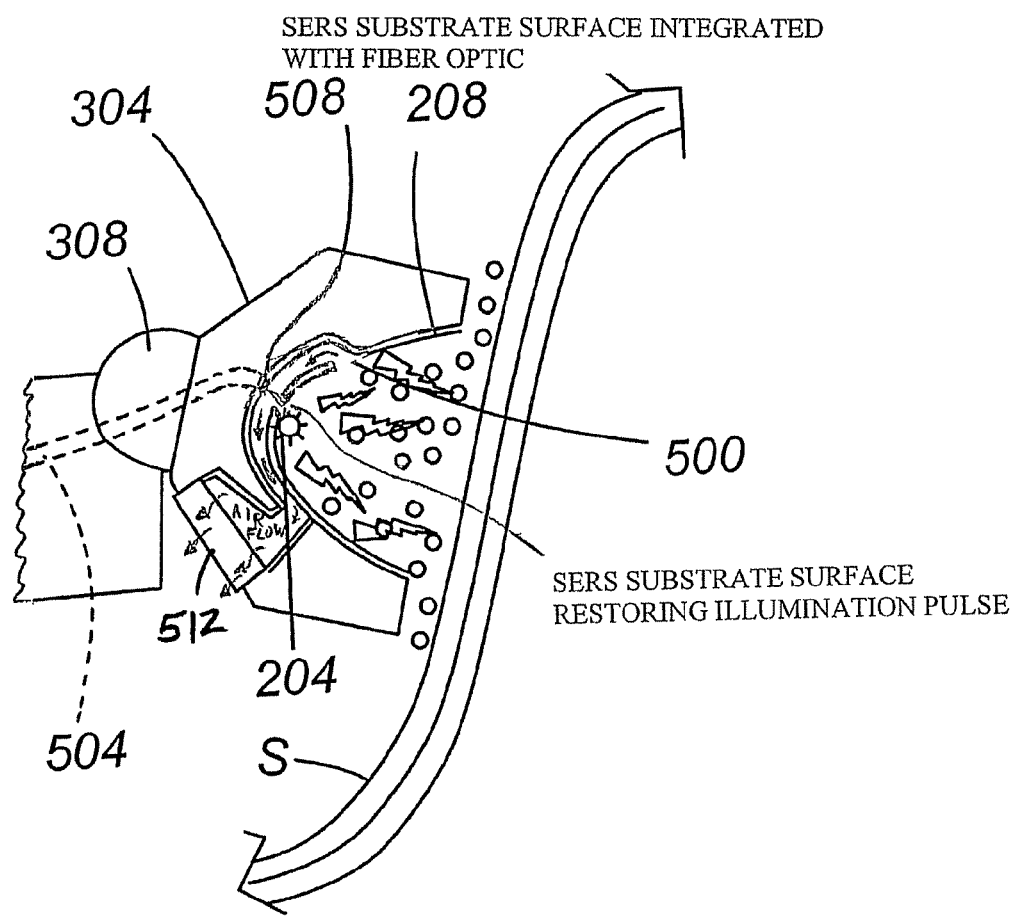
FIG. 5D is a side elevation view of a hand wand sampling device used with the apparatus shown in FIG. 4A, wherein the sampling head is shown in cut-away, and wherein a SERS substrate surface is integrated with the Raman fiber.

Referring again to the embodiment shown in FIG. 5B, the SERS substrate 508 is a spatially separate component from the Raman fiber optic 504. In accordance with at least one embodiment of the invention, the strobe 204 is positioned for providing at least a portion of energy from a pulse to the SERS substrate 508. In an alternative embodiment, and as shown in FIG. 5D, the SERS substrate 508 is integrated into the fiber optic 504, such as at the end of the fiber optic 504, and again, at least a portion of the energy from the pulse of the strobe 204 is directed to the SERS substrate 508 to refresh the SERS substrate prior to sample flow to the SERS substrate.

By combining stroboscopic signal amplification with surface enhanced Raman spectroscopy, the light from the strobe 204 may be used to accomplish two tasks. First, as described above, energy from the strobe 204 serves to liberate vapors and/or particles from the sample surface S. By amplifying the atmospheric concentration of low vapor pressure compounds and particulates over the sample surface, the stroboscopic signal amplification provides a momentary plume of chemical vapor and/or particles from the sample surface. Thus, a bulk of the illumination is preferably directed to the target sample surface S that may contain one or more chemical residuals of analytical interest. This plume, in turn, is then directed by means of ambient air movement from a pump or fan toward the SERS substrate 508 where chemicals adsorb onto the SERS substrate 508 and are analyzed by Raman spectroscopy. This plume creation and movement occurs in a time scale just longer than the time associated with cleaning of the SERS substrate surface 508 using the same stroboscopic pulse from the strobe 204. The time for plume creation and movement is typically on the order of about 200 ms or longer, and more on the order of 500 ms to 2 seconds, and may be up to 10 seconds.

However, in accordance with at least one embodiment of the present invention, prior to conveying the sample plume to the SERS substrate 508, the light from the strobe 204 may also be used to first refresh or clean the SERS substrate 508. More particularly, at least a portion of the light from the strobe 204 is directed to the SERS substrate 508 to liberate chemicals adsorbed to the SERS substrate 508, and thereby provide a refreshed or cleaner substrate surface for new material to adsorb for subsequent detection. Thus, in at least one embodiment of the invention, the process of cleaning the SERS substrate 508 is achieved by directing a fraction of the strobe illumination (photons) toward the active area of the SERS substrate. The duration of cleaning or refreshing the SERS substrate 508 occurs in less than 100 ms, and more typically, occurs on the order of less than 10 ms, and even more specifically, occurs on the order of 0.2 ms. Therefore, the duration to refresh the SERS substrate compares favorably with the sampling duration noted in the preceding paragraph. More specifically, the SERS substrate 508 is refreshed prior to conveyance of the sample plume to the SERS substrate 508.

The use of an energy source to refresh the substrate 508, and more preferably, the strobe 204, is advantageous because not all of the substrate surface area is typically used for the SERS analysis. That is, the Raman effect generally takes place only in a small area where the laser illumination from the fiber optic 504 is focused onto the SERS substrate 508. Thus, SERS detection has traditionally been hindered in application due to the length of time that the SERS substrate surface remained available for new material to adsorb to the nano-texture of the substrate. The SERS effect only applies to the adsorbed chemical species in contact with the substrate surface. Thus once materials adsorb to the surface, the surface is no longer active to new materials unless the previously adsorbed materials are removed from the surface. Therefore, the use of the strobe 204 to provide not only stroboscopic signal amplification at the sample surface, but to also provide a means for cleaning the SERS substrate is beneficial because a proper functioning SERS detector with minimal downtime is thereby achieved.

The use of stroboscopic energy is particularly advantageous for refreshing the SERS substrate due to the very short timescale and the lack of sufficient energy to heat the bulk substrate. Stroboscopic cleaning of the substrate affects just the surface-chemical interaction which will preserve the substrate features and thus preserve the Raman calibration for the life of the substrate. Substrate life may be potentially extended indefinitely, and with renewal, new blank spectral acquisitions may be taken immediately after each stroboscopic surface refresh event and prior to the arrival of the next analytical plume. The only area of the SERS substrate that is actively involved in analysis is the portion illuminated by the laser light traveling through the fiber optic. Therefore, the cleaning effect of the strobe slipstream may be enhanced by the use of a lens to focus the strobe light onto the area targeted by the fiber optic. This greatly enhances the energy delivered to the critical area of the SERS substrate.

In accordance with embodiments of the present invention, and as an alternative to using a slipstream of photons diverted from the main sampling strobe to refresh the surface of the SERS substrate 508, the surface of the SERS substrate may be renewed by energizing with a second energy source, such as a subsidiary or second strobe lamp. This secondary strobe is preferably timed to automatically flash at a predetermined interval after the main strobe 204 flashes, and before the next sample is taken. Utilization of a secondary refreshing strobe advantageously decouples the timing of the substrate renewal process from the main sampling event. An additional advantage is that the subsidiary strobe is flashed several times for each single strobe event of the main flash, thereby ensuring that the surface of the SERS substrate 508 is adequately refreshed. The subsidiary strobe may be a lower powered strobe as compared to the main sampling strobe, although this may not be necessary because the flash lamps are relatively small and lightweight. Although additional weight to the sampling system would come from additional capacitors required to drive the subsidiary lamp, these capacitors are preferably positioned remote from the flash lamp, such as in the detector housing. For the backpack stroboscopic desorption system 400, the power source 108 and capacitors may be positioned in the backpack 408. Thus, the additional weight to the overall system is trivial.

In yet another alternative embodiment of the present invention, the SERS substrate 508 is refreshed using a sudden pulse of light from a laser light emitting diode (LED). Laser LEDs are available in a range of wavelengths from the visible into the infrared. Therefore, a LED with the most effective wavelength to refresh the substrate is preferably used, with the result that the energy is most efficiently used to perform the renewal process without wasting energy in wavelengths that do not contribute to the desorption process. Pulsed LEDs are available with a power of up to 50 W or more. The pulse time is on the order 50 ns. Laser LEDs with an intrinsic focal beam magnifier with removable lenses are available. Laser LEDs are small, easily manipulated and operate at low voltages, typically at 12V. In a continuous mode, laser LEDs draw low currents of a few tens of milliamps. Thus, in accordance with embodiments of the present invention, a laser LED may be easily incorporated into the hand wand 404.

In accordance with embodiments of the present invention, a variety of optics may be used with the photon source used for cleaning the SERS substrate 508, including lenses and scanners to traverse the cleaning light over an area of the SERS substrate.

In accordance with embodiments of the present invention, the fiber optic 504 for SERS detection may comprise a bundle of fiber optics, such as a plurality of fiber optics, and in at least one embodiment, two fiber optics. For the case of this last configuration, a first fiber optic 504 may be used to provide an excitation laser light to the SERS substrate 508, and a second fiber optic 504 may be used to convey the emission light from the SERS substrate back to the detector 116.

Figure 17:
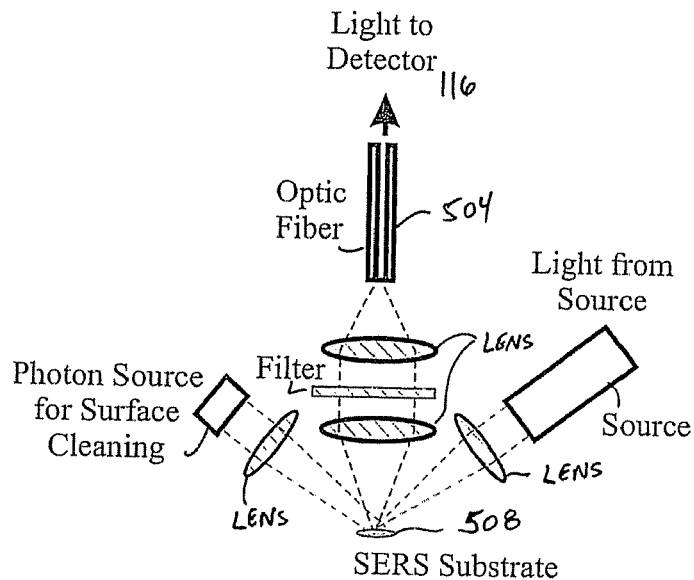
FIG. 17 is an illustration of a hand wand in accordance with embodiments of the present invention, including optical components, and showing a single optical fiber, a photon source for substrate cleaning and a Raman excitation source.
Figure 18:
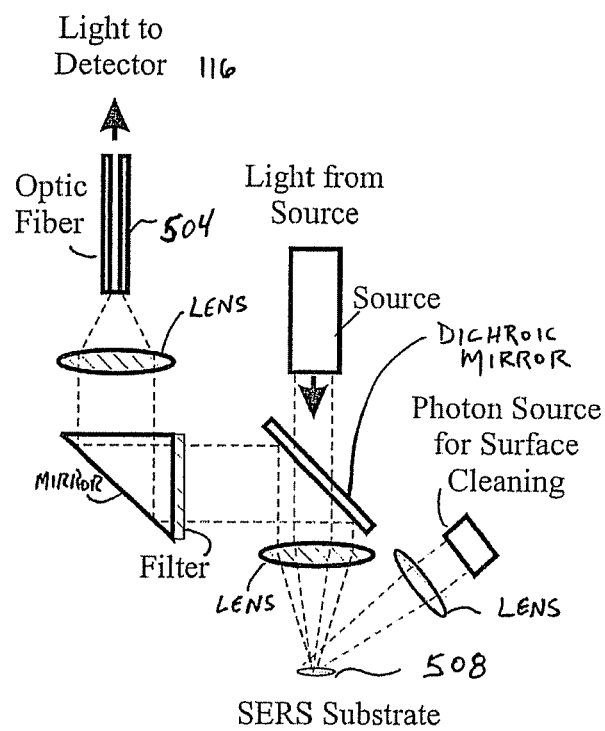
FIG. 18 is an illustration of the hand wand in accordance with embodiments of the present invention, including optical components, and showing a single optical fiber, a photon source for substrate cleaning and a Raman excitation source co-linear to at least a portion of the Raman emission light.

Referring now to FIGS. 17 and 18, SERS detection may also be accomplished using a configuration wherein a single optical fiber 504 is located proximate or in combination with the Raman excitation source. In accordance with embodiments of the present invention, a Raman excitation source, such as a laser, is positioned in a spaced-apart configuration from the detector 116. For example, for the backpack stroboscopic desorption apparatus 400, the Raman excitation source may be positioned outside of the detector 116, for example, between the backpack 408 and the sampling head 304. More preferably, the laser excitation source is located directly in the hand wand 404. With the Raman excitation source located in the hand wand 404, less excitation laser power is required because there is less Raman excitation light lost, and further, because there is reduced fluorescence as compared to using a source optical fiber 504 extending some distance back to the detector 116. For the embodiment shown in FIG. 17, the Raman source is shown exciting the SERS substrate 508 using a separate optical path. For the embodiment shown in FIG. 18, the Raman source is shown exciting the SERS substrate 508 using an optical path that is at least partially co-linear with the emission or detector light path. Both illustrations show a means for incorporating a separate SERS substrate surface cleaning photon source, that is, a separate photon emission source for cleaning or refreshing the SERS substrate surface 508.

As those skilled in the art will appreciate, hand wands 404 and other components of the various embodiments of the present invention may employ a variety of optics and/or filters, such as by way of example and not limitation, one or more lenses, dispersive elements, apertures, filters or dichroic mirrors, for focusing, passing, filtering, removing, and/or separating excitation light from emission light, and/or for otherwise manipulating the excitation light and/or the emission light. The following references, at least some of which are directed to distal end filtering, are incorporated herein by reference in their entirety: U.S. Pat. Nos. 5,112,127; 5,842,995; 5,862,273; 6,353,476; 6,558,956; 6,621,574; and 6,897,951; and U.S. Patent Application Publication No. 2005-0248758.

As noted above, another detection system appropriate for use with stroboscopic liberation or desorption is thermo-redox. In thermo-redox, the compounds and particulates liberated using stroboscopic signal amplification are collected on a pre-concentrator and pyrolyzed to release nitrous oxide, a key signature from explosive compounds. This sample collection and subsequent pyrolyzation may take place in the hand wand 404, if desired. The evolved nitrous oxide is then conveyed using tube 212 to the detector 116 located in backpack 408, where detection of compounds can be conducted using proprietary and conventional methods. For purposes of enablement, a Scintex EVD2500 is a ruggedized, hand portable unit that is believed to be appropriate for adaptation and use with a stroboscopic liberation or desorption device of the present invention.

As noted above, yet another detection system appropriate for use with stroboscopic liberation or desorption is chemiluminescence. In chemiluminescence, the compounds and particulates liberated using stroboscopic signal amplification are, like thermo-redox, collected on a preconcentrator and pyrolyzed, but then exposed to a chemical reaction that creates an excited state of nitrous oxide that is detected using a very sensitive photometer. As with thermo-redox, it may be possible to move the pyrolysis produce to a backpack mounted system that performs the chemical reaction and optical detection. As with thermo-redox, chemiluminescence cannot identify the detected compounds unless the sampled vapor is subject to gas chromatography prior to pyrolysis.

In accordance with at least some embodiments of the present invention, the detector 116 may be mounted in a permanent location, such as in the vicinity of a baggage conveyor, as discussed below. Alternatively, a vehicle, such as a van may be adapted for transporting a detector 116 in accordance with embodiments of the present invention. For such configurations, trace detection of compounds such as explosives may be conducted using a mass spectrometer detector. Thus, there a variety of detection systems adaptable for use with stroboscopic desorption, including both portable and stationary detection systems.

In a separate aspect of the invention, a stroboscopic desorption device is provided for automatically examining baggage and/or packages. In one embodiment, a stroboscopic desorption device is used to screen luggage, packages, boxes, bags, (herein also collectively referred to simply as "baggage" or "luggage") as the luggage passes along a conveyor belt, conveyance mechanism, or other security check point. The device is positioned to bring a strobe desorption unit into sampling proximity with the surfaces of the luggage, thereby allowing multiple desorption events on each piece of luggage. As described herein, the strobe desorption unit may utilize one or more sensors.

Referring now to FIG. 6, and in accordance with at least one embodiment of the present invention, a first possible configuration of an automatic stroboscopic desorption and detection system 600 is shown for screening luggage and/or packages. The automatic stroboscopic desorption and detection system 600 preferably includes a conveyance system, such as one or more rollers, and/or one or more other continuous or endless sample feed mechanisms, such as a conveyor belt 604, that moves in the direction of arrow $A_1$, or otherwise conveys samples in the direction $A_1$. For the embodiment shown in FIG. 6, the conveyor belt 604 is used to automatically place test samples, such as packages, bags, and/or luggage, in testing proximity with one or more stroboscopic desorption devices 608. For the arrangement shown in FIG. 6, three stroboscopic desorption devices 608a, 608b and 608c are shown.

In the first configuration, the system 600 includes moveable radiation sources that extend over the width of a conveyor belt 604 that moves the luggage and/or packages. In at least one embodiment, a flap or hinged arm 612 is suspended from an upper hinge 616 that is separated a sufficient distance from the conveyor belt 604 to accommodate the largest pieces luggage L, bags or packages that may be encountered. The stroboscopic desorption devices 608a, 608b and 608c are preferably biased in a downward position to intercept the luggage L as it passes under the stroboscopic desorption devices 608a, 608b and 608c. Since the positioning apparatus preferably includes the hinged arm 612 that accommodates different size packages or luggage L, the hinge 616 allows rotation of the hinged arm 612 such that the stroboscopic desorption devices 608a, 608b and 608c can move up and down as a package or piece of luggage moves under it.

In at least one embodiment of the invention, the bottom of the flap or hinged arm 612 is preferably in sampling proximity with the conveyor belt 604, and the hinged arm 612 makes an oblique angle, such as an angle of approximately 45°, with the conveyor belt 604, such that the hinged arm 612 points downstream of the conveyor belt 604. In accordance with at least one embodiment of the present invention, there is a second hinge 620 at the trailing edge of the flap or hinged arm 612, to which is attached a second flap 624 that carries the desorption strobes and the analytical sensors if used, such as the SERS substrate surface. In at least one embodiment, this second flap 624 is the width of the conveyor belt 604 and is sized to allow the strobe 204 and SERS substrate surface 508 to screen the leading edge of luggage L that is lying flat.

The stroboscopic desorption devices 608a, 608b and 608c are consistent with the stroboscopic devices discussed earlier, and include a strobe 204 and detector 116 in communication with the sampling head of the stroboscopic desorption devices 608a, 608b and 608c. Of course, for a luggage conveyor or similar system located in a permanent structure with electrical power, the stroboscopic desorption devices 608a, 608b and 608c may be powered by AC electrical power. In addition, the liberation components, such as the sample head 304 and strobe 204, may be physically separated from the detector 116. For example, stroboscopic desorption devices 608a, 608b and 608c of FIG. 6 may provide a collective sample to a single detector. More particularly, for this and other embodiments of the invention, instead of immediately detecting the liberated sample, the liberated material may be collected on a preconcentrator (such as a length of packed column or a cooled piece of open tubular column) and later in time and/or at a different location, the collected material may then be desorbed for detection. Alternatively, the stroboscopic desorption devices 608a, 608b and 608c of FIG. 6 may each have their own detector 116. As shown in FIG. 6, if each of the stroboscopic desorption devices 608a, 608b and 608c have their own detectors 116, they may also be supplied with an individual alarm system 628 for notifying security personnel of the suspected piece of luggage L.

In at least one embodiment of the invention, an automatic sample conveyance and stroboscopic detection system may comprise a means for physically isolating, separating, and/or ejecting a suspected sample from the main conveyance mechanism, such as a suspected piece of baggage from a conveyor system, for quarantine or other special handling. For example, the conveyor belt 604 of system 600 may include one or more holding bins for detaining and/or quarantining a suspected piece of baggage after an initial detection using a detector, such as stroboscopic desorption device 608a. Such a feature may include a holding bin or isolation area positioned proximate or at a distance from the main conveyor belt 604, such that the suspected piece of baggage is automatically separated for further analysis and/or evaluation, such as by inspection by authorized personnel.

Referring now to FIGS. 7A-7C, a multi-hinge stroboscopic desorption system 700 is shown wherein the stroboscopic desorption device 704 is shown in its various positions. FIG. 7A shows the stroboscopic desorption device 704 in its at rest position with a piece of luggage L approaching it in direction arrow $A_1$. FIG. 7B shows the stroboscopic desorption device 704 rising along a side of the piece of luggage L. FIG. 7C shows the stroboscopic desorption device 704 along the top of the piece of luggage L.

As with the automatic stroboscopic desorption and detection system 600 discussed above, the multi-hinge stroboscopic desorption system 700 uses an apparatus, such as a conveyor belt, for automatically moving the sample item, such as a piece of luggage L, under the stroboscopic desorption device 704. The stroboscopic desorption device 704 preferably resides on a first flap 720 that is connected to a first hinge 708 that is capable of rising over the piece of luggage L. The first hinge 708 is interconnected to a preferably stationary second hinge 712, such as by second flap 716. Use of the first hinge 708 allows the sample head of the stroboscopic desorption device 704 to contact or come into sampling proximity with the sloped sides of the luggage L, while the second hinge 712 anchors the stroboscopic desorption device 704 while still accommodating rises in the stroboscopic desorption device 704 due to the size and shape of the luggage L. The stroboscopic desorption device 704 is consistent with the stroboscopic desorption devices discussed previously, and allows the surfaces of the subject article or luggage L, to be tested with little or no damage to the surface of the article.

In use, the leading edge of luggage L traveling along the conveyor encounters the second flap 716 and lifts it. The stroboscopic desorption device 704 positioned along a first flap 720 hangs downwards bringing the strobe 204 and any attendant senor, such as the SERS substrate surface 508, into sampling proximity with the leading side of the luggage L, such as is shown in FIG. 7B. In accordance with at least one embodiment, lifting the first flap 716 serves to actuate the sensor and the strobe 204 that flashes, as for example at 2 Hz. When the piece of luggage L, baggage reaches the first hinge 708, the first flap 720 is lifted up and travels across the upper surface of the piece of luggage L.

Figure 8:
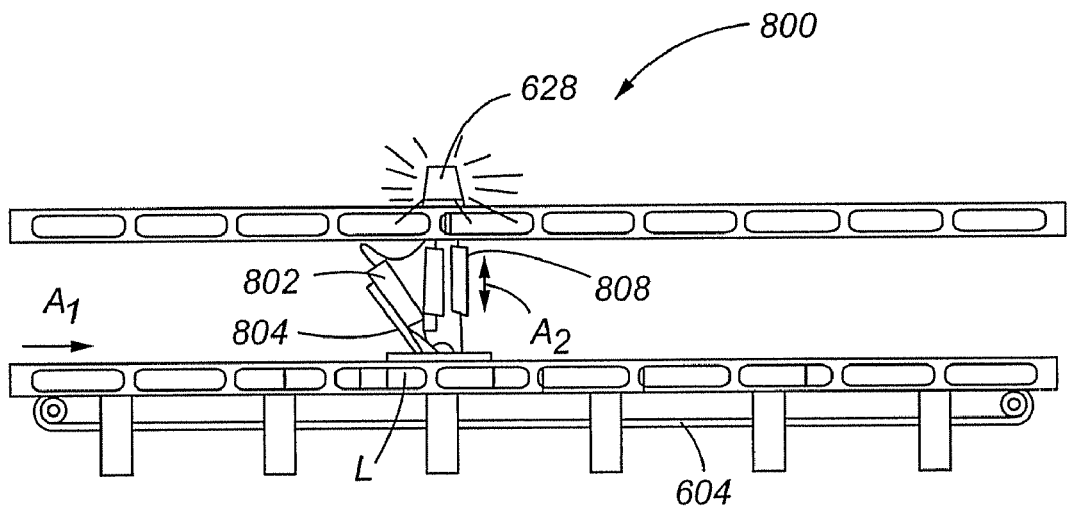

Referring now to FIG. 8, in an alternate embodiment of the present invention, an automatic stroboscopic desorption system 800 comprises a stroboscopic desorption device 802 having a strobe 204 and any attendant analytical sensor, such as SERS substrate surface 508 and fiber optic 504. The stroboscopic desorption device 802 is carried on a skid 804 that travels up and over the luggage L as it moves along the conveyor 604. A means for vertically lifting and lowering the system as per arrow $A_2$ is used to raise and lower the skid 804, wherein such means for raising a lowering may include a variety of mechanisms, such as hydraulic-damped springs, a pressure activated lift-assist, and/or optical activated lift-assist 808.

Figure 9A:
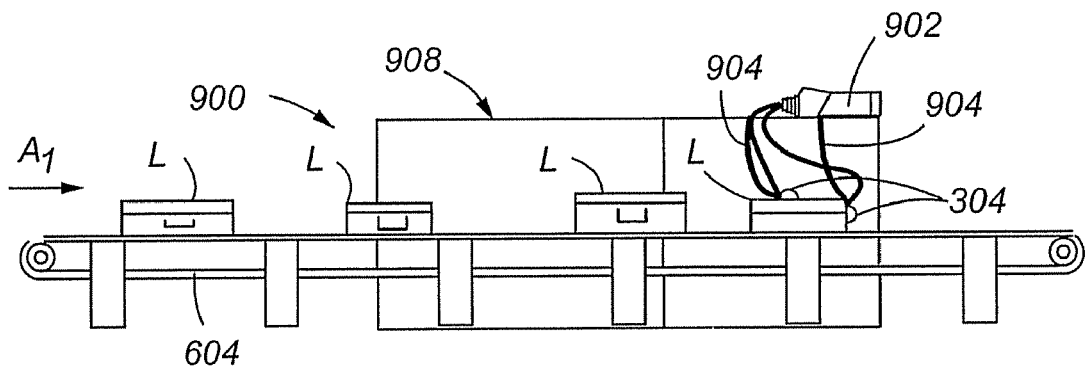

Referring now to FIG. 9A, yet an alternate embodiment of an automatic stroboscopic desorption system 900 is provided for use with X-ray machines at, for example, airline security check points. In at least one embodiment of the invention, the system 900 preferably uses a stroboscopic desorption device 902 having a plurality of strobes 204, and if applicable, sensors, such as SERS substrate surface 508 and fiber optic 504, that are carried on the flexible straps 904 that are on the entrance of a X-ray machines that protect passengers and TSA personnel from radiation emitted by the X-ray machine 908. As the luggage L passes through the curtain of straps 904, they drape over the luggage L pulling the sampling head 304 including strobe 204 and the attending sensors across the surface of the luggage L.

Referring now to FIG. 9B, and in accordance with at least one embodiment of the present invention, a stroboscopic desorption device 912 is shown wherein a plurality of sampling heads 304a-c are operatively interconnected to a single detector 116. The device 912 preferably includes a plurality of corresponding number of tubes 212a-c and/or fiber optics 504a-c, respectively, for transporting an airborne sample or conveying sample data to the detector 116. A valve 916 or other switching means may be used for isolating the sampling head and associated tubing or fiber optics for communication with the detector 116. Alternatively, the detector 116 may obtain sample data from all sampling heads 304a-c simultaneously. A detector using a plurality of sampling heads 304 is applicable to a number of embodiments described herein, including those for screening luggage or packages.

Referring now to FIG. 9C, and in accordance with at least one embodiment of the present invention, a graph 920 is shown that illustrates use of a means of isolating sample detection to an individual sampling head 304a-c. More particularly, and by way of example and not limitation, for a system using a pump or fan for creating a preferential air or gas flow within a tube 212a-c, the pump or fan is preferably switched "on" to provide suction to a first sampling head 304a, then the pump or fan is allowed to continue operating during period Δt to clear the common tubing 212 and/or detector 1116, then the fan or pump is switch "on" to provide suction to a second sampling head 304b, and again, then the pump or fan is allowed to continue operating during period Δt to clear the common tubing 212 and/or detector 116, and then the pump or fan is preferably switched "on" to provide suction to a third sampling head 304c, then the pump or fan is allowed to continue operating during period Δt to clear the common tubing 212 and/or detector 116. This is merely an example of an operation pattern. Accordingly it is to be understood that the system may be modified in a variety of ways, including re-ordering the switching, providing a different mechanism for flushing or clearing the sample head 304a-c and its associated tubing 212a-c. Furthermore, depending upon the detector used, for example, if fiber optics 504 are used with no tubing 212, little or no clearing or flushing may be required.

Figure 10:
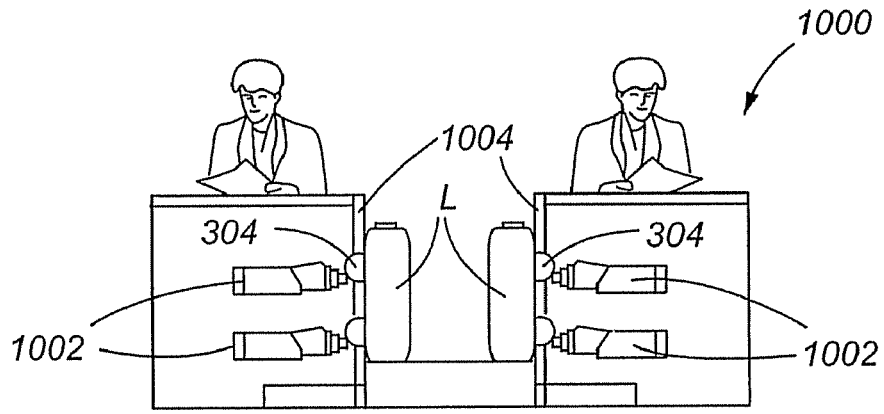
FIG. 10 is a view of another automated stroboscopic sampling systems in accordance with embodiments of the present invention.

Referring now to FIG. 10, in yet still another embodiment of the invention, an automatic stroboscopic desorption system 1000 is provided for use with airline check-in counters, or other similar package or luggage check-in stations. For the check-in automatic stroboscopic desorption system 1000, one or more stroboscopic desorption devices 1002 may be used, with the sampling head 304, including the strobe 204 and any attendant sensors built in to the sides of the scale or counter 1004. When the luggage L is placed next to the sampling head 304, the automatic stroboscopic desorption system 1000 allows the stroboscopic desorption device 1002 to screen the luggage L of compounds of interest, including explosives and/or drugs as the passenger is being checked-in.

In accordance with embodiments of the present invention, a luggage or package detection system may be coupled with the various automatic stroboscopic desorption systems 600, 700, 800, 900, 1000 discussed above. More particularly, the luggage or package detection system comprises a means for identifying the presence of a piece of luggage or a package so that the automatic stroboscopic desorption system does not trigger (or flash) until a luggage or package is known to be present in the sampling vicinity of the automatic stroboscopic desorption system. The luggage or package detection system may comprise a variety of technologies, including by way of example and not limitation, weight sensing devices, motion detectors and other optical sensors, and radar. The use of a luggage or package detection system in combination with an automatic stroboscopic desorption system is anticipated to improve longevity of the automatic stroboscopic desorption system.

Figure 11:
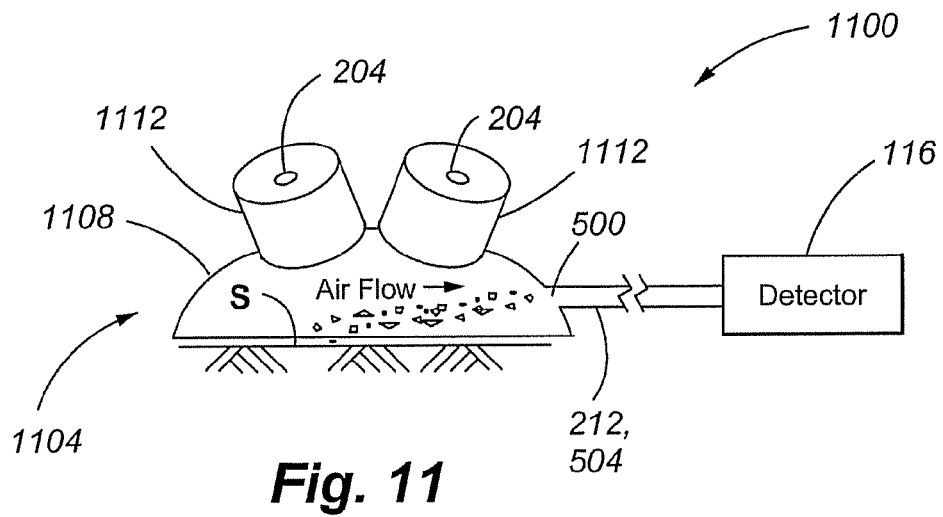
FIG. 11 is a side elevation view of a sampling head in accordance with at least one embodiment of the present invention.

Referring now to FIG. 11, a stroboscopic desorption system 1100 is shown that comprises sampling head 1104 having a shroud 1108 with a plurality of strobes 204. In at least one embodiment, each of the strobes 204 resides within a reflector 1112, wherein at least a portion of the reflector 1112 has a parabolic shape for directing the light from each strobe toward a common sample target area under the shroud 1108. This type of sampling head 1104 provides a means for providing multiple simultaneous energy sources directed at the same area of the sample surface S, or alternatively, it provides a means for temporally staggering the demand on a single strobe 204, thereby allowing each strobe capacitor to recharge, while the other strobe is tasked with radiating the sample surface S. The shroud 1108 preferably includes a port 500 leading to a sample tube 212 or fiber optic 504, that in turn leads to a detector 116.

Figure 12:
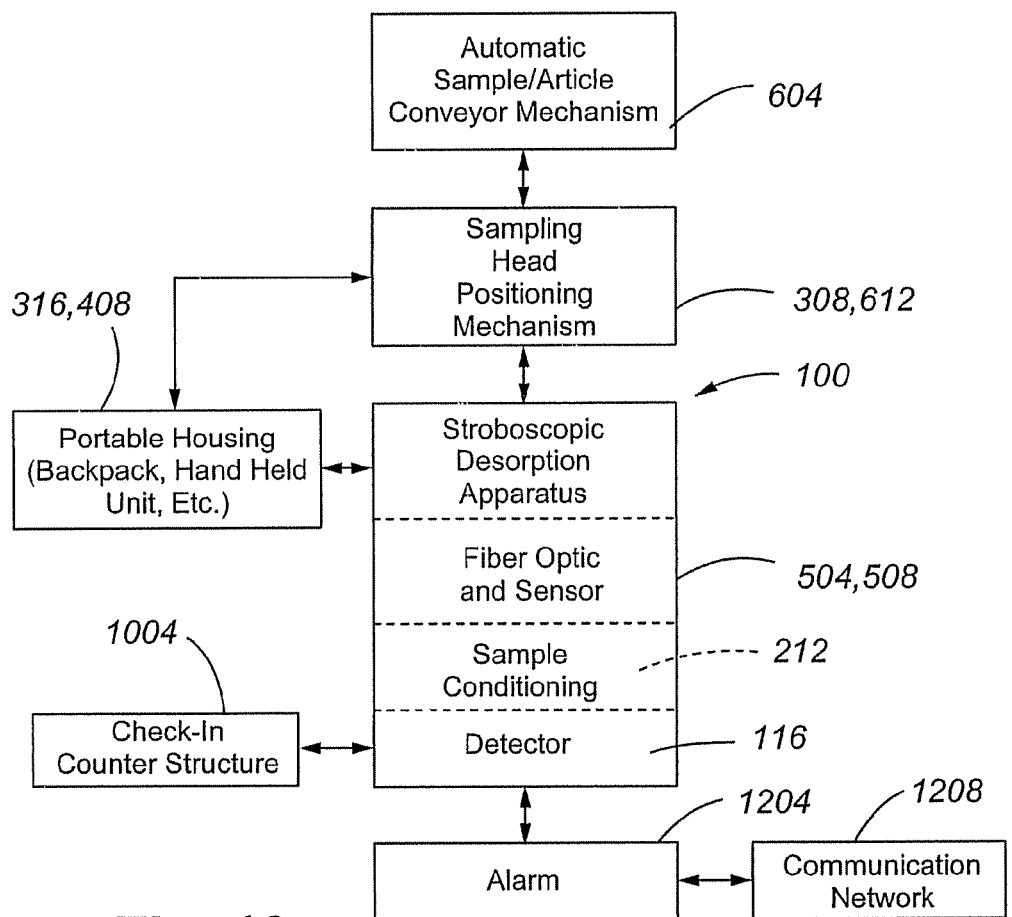
FIG. 12 is block diagram depicting several possible configurations of components from various embodiments of the present invention.

Referring now to FIG. 12, a block diagram showing several possible system configurations 1200 is illustrated. A stroboscopic desorption apparatus 100 may be combined with a fiber optic 504 and sensor 508 for transmitting sample information to a detector 116. The apparatus may also use sample conditioning, such as along a tube 212 to keep any vaporized portion of the sampled compounds from condensing prior to reaching the detector 116. In accordance with embodiments of the present invention, the sample conditioning may comprise a heated conduit or tube 212 to transport the collected sample to the detector. In at least one embodiment, the temperature of the heated conduit is at least the condensation temperature of the material. Where used, preferably the temperature of the heated conduit ranges from about 100° C. to about 250° C. In at least one embodiment, the heated conduit comprises a glass and/or ceramic surface adjacent the transported sample. In addition, when used, the heated conduit may comprise silanizing agent and/or a substantially nonpolar surface adjacent the transported sample.

Other possible system configurations include use of a sampling head positioning mechanism for placing the strobe in sampling proximity with a sample surface, wherein such mechanisms include a swivel mechanism 308 or hinged arm 612. In addition, an automatic sample/article conveyor mechanism such as a conveyor belt 604 may be used to place the sample under the strobe desorption apparatus. In accordance with embodiments of the present invention, the device may comprise a housing 316 or backpack 408 for providing a portable screening device, wherein the portable screening device is preferably a self-contained unit, including a power source 108 and a detector 116. Portions of the portable unit may include a sampling head, such as a hand-held wand interconnected to a backpack, wherein the wand portion includes a sampling head positioning mechanism, such as swivel mechanism 308. Alternatively, the apparatus may be stationary, such as located in a check-in counter 1004 at an airport terminal.

Referring still to FIG. 12, an alarm 1204 may be interconnected to the detector 116 associated with any of the embodiments described herein. In at least one embodiment, the alarm 1204 is either hardwired and/or wirelessly networked to a communication network 1208 for contacting authorities. Thus, a variety of different possible configurations are possible. In accordance with embodiments of the invention, the alarm 1204 and/or communication network 1208 may comprise wired transmission means, at least one wireless transmitter, and/or electronic recording means of the detection information. The detection information may be intermittently or continuously provided by the detectors of the present invention, such as the backpack stroboscopic desorption apparatus 400, to a separate location. This functionality provides for separate real-time or subsequent monitoring of screening results by offsite and/or spatially separated personnel (or monitoring by computer automation), and/or single or duplicate maintenance of records of testing results away from the actual detector unit in the event of the need, such as, for example, a security breach resulting from an infiltration of the security force by one or more opposition personnel. Such application may be used in a variety of situations, such as screening efforts at security checkpoints. The monitoring may further comprise ground positioning technology, as well as video recording of the subject and/or sample surface using a means for obtain video information, wherein this may comprise digital pictures taken directly by one or more computer chips positioned in the wand or other portion of the detector apparatus. Thus, in accordance with embodiments of the present invention, a small camera, such as a micro-camera, may be used to take one or more pictures of the sampling surface, and furthermore, operate alone or in conjunction with a proximity sensor. The system may further incorporate logic that ensures that a unique surface is being analyzed in sequential activations, along with identifying the nature of the screened surface. This technology may be particularly useful for post-screening review of personnel and objects screened, with time tracking of the pictures/video to the detector results. Furthermore, embodiments of the present invention may be mounted on a remotely and/or wirelessly controlled platform or robot, wherein a camera is used with one or more motors to position the sampling head on a surface of interest. Such configuration may be particularly suited to objects (or people) considered of significant risk to screening personnel.

In accordance with embodiments of the present invention, a preferred sequence of operation is used that is directed to stroboscopic signal amplification operation, sample collection, and subsequent data analysis. Embodiments may also include a means for rapid compound identification and data buffering while data collection continues.

In accordance with embodiments of the present invention, the system may use EEPROM, non-volatile ID chips that allow the system to automatically recognize the major interchangeable parts, such as a backpack Raman system 400, a signal cable 416, and a stroboscopic hand wand 404 and user interface 128.

Thus, in accordance with embodiments of the present invention, a stroboscopic desorption system is provided, the system including a detector 116 and a hand wand 404. The detector 116 may be positioned at a stationary location, or on a portable or mobile platform, such as a cart. Alternatively, the detector 116 may be positioned within a portable configuration that can be carried by a user, such as a backpack 408. Features of the system, such as the backpack stroboscopic desorption apparatus 400, preferably include a power source 108, and may further include a signal cable 416 that carries power electrical/communication wiring and/or one or more fiber optics 504, wherein the signal cable 416 is positioned between the detector 116 and the hand wand 404. The one or more fiber optics 504 provide a means for communication between the hand wand 404 and the detector 116. In accordance with embodiments of the present invention, the hand wand 404 may comprise a sampling head 304 that includes a shroud 1108. The hand wand 404 or sampling head 304 preferably comprise a pump or a fan 512 to provide air or gas flow through the sampling head 304, thereby directing a sample plume generated by the strobe 204 to a SERS substrate 508 located in the hand wand 404. The pump or fan 512 also provides for venting the shroud 1108 and cooling one or more of the strobe 204 and the SERS substrate 508. The hand wand 404 also preferably includes a user interface, such as a screen 328, speaker, and/or vibrator for signaling the operator of a positive detection of a compound of interest, such as an explosive or drug. In addition, embodiments of the present invention include means for cleaning or refreshing the SERS substrate 508. In one preferred embodiment, at least a portion of the strobe light is directed to the SERS substrate 508 for desorption of compounds from the substrate surface prior to the plume from the sample surface contacting the substrate. Of course, while the system just described is configured for having the Raman system detector 116 separated from the hand wand 404 and SERS substrate 508 using a signal cable 416 including one or more fiber optics 504 and potentially other electrical leads, it is to be understood that the present invention also includes and encompasses full integration of the entire system into a portable or stationary system without the signal cable 416 and hand wand 404. For example, and without intending to limit the scope of possible configurations encompassed by the present invention, the system could reside in a housing located on a counter or on a portable cart or vehicle, wherein an item of interest or sample is placed inside a screening container or otherwise in sampling proximity with one or more sampling heads.

EXPERIMENTAL DATA

The following experimental data includes high-energy strobe results (Examples 1 and 2; provided for comparison purposes) and low-energy strobe results (Example 3, provided in support of the present invention).

Example 1

The apparatus used included a strobe light and an aluminum box with a sealed glass cover in which a sand sample was located. A valve was used to select a bypass or passage through the sample to a gas chromatograph. The sand sample included 1 ppm of triethyl phosphate and 1% by weight water. Triethyl phosphate is a high boiling point material, having a boiling point of 215° C.

A stream of air, having a flow rate of 64 ml/minute, was passed through the bypass and into the gas chromatograph with an open 3 mm stainless steel column and flame photometric detector fitted with a 526 nm optical filter for phosphorous detection. The baseline with the gas passing through the by pass was observed.

The gas flow was then switched to pass through the box and over the sand sample. There was no inflection in the baseline, indicating that the vapor pressure of the triethyl phosphate was too low to be detected. The detection limit for phosphorous is about $10^{-11}$ g/sec.

The strobe light was then placed over the cell and flashed. The detector showed an immediate response as a large peak. The strobe light was a Speedotronic™ 2403™ strobe head with a Speedotronic™ Blackline™ power supply, delivering 2,400 watt-seconds of power. A strobe head of this size can generate a very large electrical disturbance and, to ensure that the detector was, in fact, responding to the phosphorus and not an electrical signal, the glass of the cell was covered with cardboard and the strobe was again fired. There was no response from the detector.

Figure 14:
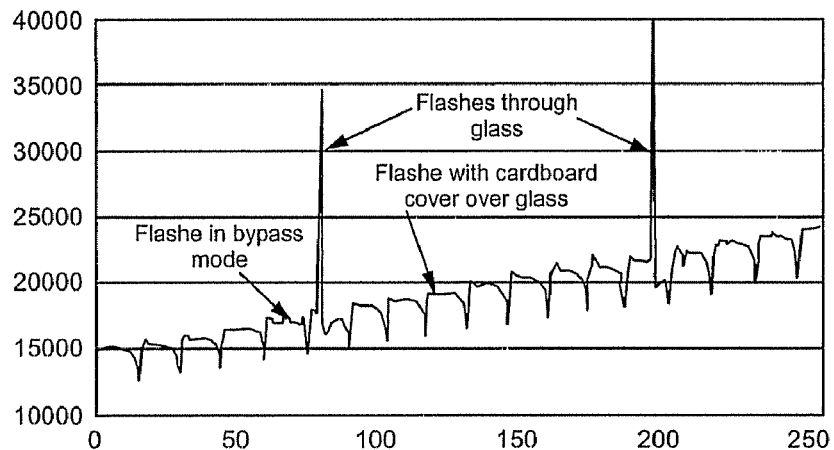
FIG. 14 is a plot of intensity (ion count) (vertical axis) versus scan number (horizontal axis) for an experiment as discussed in Example 1 herein.

The cover was removed from the box and the strobe was again fired. There was another large response from the detector. The output of this experiment is presented in FIG. 14. Referring to FIG. 14, the periodic signal from the detector is due to the thermal cycling of the heater in the detector.

This experiment shows that the test apparatus can successfully detect extremely low concentrations of a high boiling point substance.

Example 2

The apparatus included a 1,200 Joule strobe lamp, a heated inlet, an atmospheric pressure chemical ionization tandem mass spectrometer, and a test rig containing TNT impregnated sand. The test rig was a cylindrical test cell with a glass cover. Air was drawn through the apparatus and into the inlet system of the spectrometer. The spectrometer was set to monitor the response of the molecular ion of TNT at a mass to charge ratio (m/z) of 227.

Figure 15:
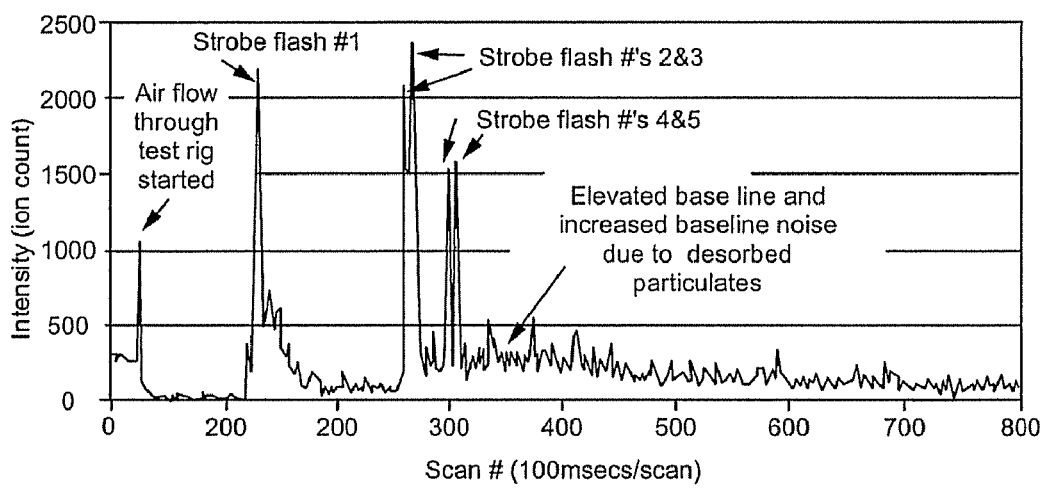
FIG. 15 is a plot of intensity (ion count) (vertical axis) versus scan number (horizontal axis) for an experiment as discussed in Example 2 herein.

The results of one of these experiments are presented in FIG. 15. The mass chromatogram of FIG. 15 illustrates the release of a series of sharply defined plumes of vapor in response to the influx of energy from the strobe. It is also apparent that the baseline after the first strobe flash becomes elevated and analytically much noisier. It is assumed that this increase in the baseline activity is due to explosive carrying particulate material that has been released from the soil by the strobe. This activity increases with the subsequent flashes due to the sand being dried by the heat of the strobe and becoming more prone to release fine particulates.

Example 3

In view of the strong response that was observed with high-power (+1,200 J) strobes, it was decided to test the response of lower-powered strobes in the range of 3-6 Joules. Although the output from these small strobes is much less, the area that they illuminate is also much smaller so that the Joules/cm$^2$ may still be substantial from a signal amplification perspective, but not damaging to the subject surface.

The sensor used for these tests relies upon a fluorescent polymer that is quenched by nitroaromatics such as TNT. The response of the sensor when a nitroaromatic is detected is a quench in the fluorescent response, resulting in a trough in the baseline. The sensor is very sensitive and detection limits as low as one femtogram are claimed.

A series of tests were conducted using pieces of canvas that had been impregnated with varying quantities of TNT. The TNT was introduced onto the canvas from PTFE strips that had been prepared by pipetting TNT in solution onto the strips, and allowing the solvent to evaporate. The residual solid TNT was then transferred to the canvas by carefully wiping the explosive onto the cloth. The canvas strips were then exposed to a flash from a 4.2 Joule strobe, while drawing the evolved plume into the sensor. The tests were repeated in triplicate and with varying quantities of TNT.

Figure 16:
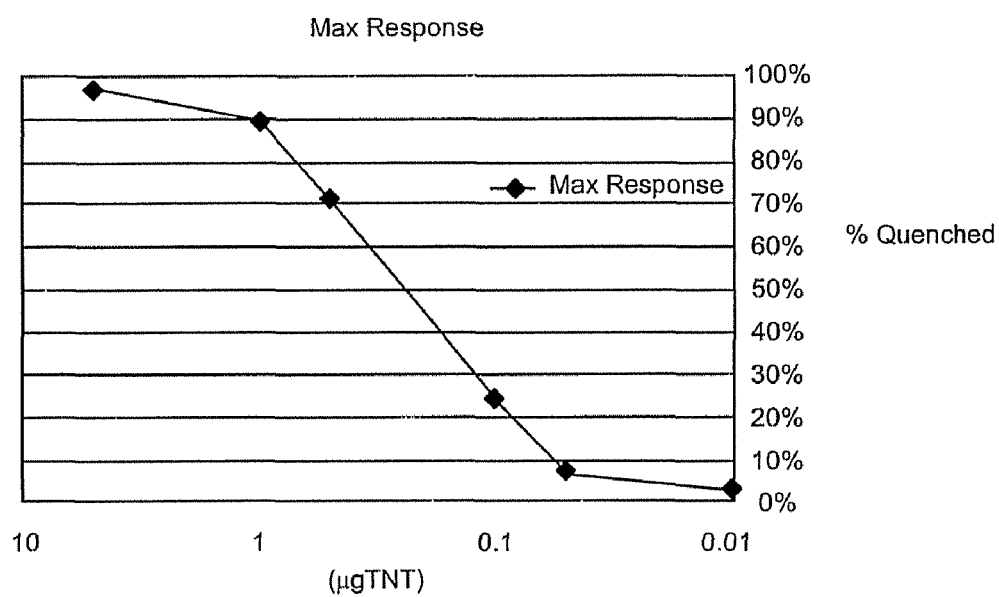
FIG. 16 is a plot of percent quenched (vertical axis) versus sample concentration of TNT in units of micrograms (horizontal axis) for an experiment as discussed in Example 3 herein.

The results of the tests are shown in FIG. 16. It can be seen that with 5 µg or 1 µg of TNT, the fluorescence is almost totally quenched and, therefore, the detector is saturated. The detection limit from these tests was approximately 0.01 µg of TNT. This was a surprising and unexpected result from a small strobe, because earlier work had shown that decreasing the power of a high-powered strobe from 2,400 J to 1,200 J resulted in a dramatic decrease in the response from the detector.

In summary, stroboscopic signal amplification provides a short interval of broad-band light energy to momentarily create an enrichment of vapor and particulates above a sample surface. By using extremely short bursts of stroboscopic light to provide sufficient but substantially non-damaging energy at the sampling surface, the detection limits of traditional trace vapor detector systems may be increased by two or more orders of magnitude. As a result of the mechanism of stroboscopic signal amplification, the vapor mode detection of detection instrumentation is able to momentary sample both an increased vapor concentration and liberated micron-sized particles from the surface under study. Fine particulates are known to carry enhanced concentrations of contaminants such as explosives and drugs. Thus, by employing stroboscopic enhanced trace chemical detection, there is no need to operate a trace chemical detector in a traditional particle mode employing the manual steps of swiping a surface and placing the swipe in a pulsed thermal desorber. Embodiments of the present invention include, but are not limited to, portable stroboscopic desorption devices for screening people or vehicles at checkpoints or crime scenes, as well as stationary stroboscopic desorption devices that may be used in a variety of ways, including screening of luggage at an airport. Embodiments comprise the application of sufficient energy at the sample surface to increase detection levels of targeted compounds, while causing limited or no damage to the sample surface. In addition, embodiments of the present invention include combining specific detector technology, such as, but not limited to SERS, with stroboscopic signal amplification. Embodiments further comprise the use of a strobe or another energy source to assist in maintaining the integrity of the SERS substrate, such as a SERS substrate located in a hand wand that is interconnected to the detector processor. Thus, the stroboscopic enhancement acts to not only improve the sampling of the SERS detector, but also refreshes the SERS substrate for maximum signal to noise and substrate longevity.

A number of variations and modifications of the invention can be used. It is possible to provide for some features of the invention without providing others. For example in one alternative embodiment, the system is used to detect low boiling point or high vapor pressure materials. In another alternative embodiment, multiple detectors can be used simultaneously or near simultaneously to detect different target substances.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights that include alternative embodiments to the extent permitted, including alternate, interchangeable and/or equivalent structures, functions, ranges or steps to those claimed.

What is claimed is:

1. A method for detecting, by Raman spectroscopy, a trace chemical from a target surface, the method comprising:

(a) pulsing a strobe to contact broadband light with the target surface, wherein the broadband light liberates the trace chemical from the target surface, wherein the broadband light has a wavelength range of from about 300 nm to about 2 microns, wherein the strobe has an initial discharge peak interval of less than about 100 µs, and wherein the strobe light, during the pulse, illuminates the target surface with radiation having an energy level of from about 0.4 to about 5 $J/cm^2$ of target surface;
    (b) collecting the trace chemical in an airborne sample;
    (c) causing, by a Raman excitation source, a surface enhanced Raman scattering of the trace chemical; and
    (d) detecting, from the Raman scattering and by a detector, the trace chemical, wherein the Raman excitation source and detector are in separate units connected by a fiber optic component.

2. The method as claimed in claim 1, wherein the airborne sample comprises one or more of a particle and a compound.

3. The method as claimed in claim 1, further comprising moving the target surface under the strobe prior to the pulsing step.

4. The method as claimed in claim 1, wherein the collecting step comprises the substep of providing at least one of a pump and a fan to pull the airborne sample to a SERS substrate before the detecting step.

5. The method as claimed in claim 1, further comprising activating an alarm after the detecting step.

6. The method as claimed in claim 1, wherein the trace chemical comprises a high boiling point and/or low vapor pressure, and wherein the trace chemical comprises is at least one of an explosive, an explosive related compound, a chemical warfare agent, a drug, a toxic industrial compound, and derivatives thereof.

7. The method as claimed in claim 1, further comprising placing a hand wand in sampling proximity of the target surface prior to the pulsing step.

8. The method as claimed in claim 7, wherein the hand wand includes the strobe and a SERS substrate for adsorbing the trace chemical and for conducting at least a portion of the surface enhanced Raman scattering.

9. The method as claimed in claim 8, further comprising irradiating the SERS substrate by a Raman excitation source to detect trace chemicals on the SERS substrate and thereafter cleaning the SERS substrate using photons.

10. The method as claimed in claim 9, wherein the photons of the cleaning step are emitted from the strobe.

11. The method as claimed in claim 9, wherein the photons of the cleaning step are emitted from a laser other than the Raman excitation source.

12. The method as claimed in claim 9, wherein the photons are emitted from a laser LED located in the hand wand.

13. A system for detecting, by Raman spectroscopy, at least one chemical located on a target surface, the system comprising:

(a) a first strobe for imparting energy to the target surface, wherein said energy liberates the at least one chemical from the target surface, wherein the energy is broadband radiation, wherein the broadband radiation has a wavelength range of from about 300 nm to about 2 microns, wherein the first strobe has a full light duration of up to about 3,000 µs, and wherein, during the full light duration, the first strobe illuminates the target surface with radiation having an energy level of from about 0.4 to about 5 $J/cm^2$ of target surface; and
    (b) a SERS substrate operable to adsorb the at least one chemical liberated from the target surface; and (c) a detector operable to detect the at least one chemical, the detector being in operative communication with the SERS substrate by a light transmission component, wherein the SERS substrate and a Raman excitation source are located in a first unit and the detector is located in a second unit, and wherein the first and second units are spatially dislocated.

14. The system as claimed in claim 13, wherein the light transmission component is a fiber optic component, wherein the first strobe provides between about 0.4 to 5 Joules of energy per square centimeter of the target surface area as measured at the target surface.

15. The system as claimed in claim 13, further comprising an optical path between said first strobe and said SERS substrate, wherein photons emitted from said first strobe clean at least a portion of said substrate prior to the at least one chemical being adsorbed on to said SERS substrate and wherein said cleaning being distinct from irradiation of the SERS substrate by the Raman excitation source.

16. The system as claimed in claim 13, further comprising a photon emitter other than said first strobe, said photon emitter providing at least a pulse of photons for impinging and cleaning said SERS substrate, said impinging and cleaning being distinct from irradiation of the SERS substrate by the Raman excitation source.

17. The system as claimed in claim 16, wherein said photon emitter comprises a second strobe.

18. The system as claimed in claim 16, wherein said photon emitter comprises a laser LED other than the Raman excitation source.

19. The system as claimed in claim 13, wherein said strobe and said SERS substrate and a Raman excitation source are located within a hand wand.

20. The system as claimed in claim 13, wherein said strobe and said SERS substrate are both located within a hand wand.

21. The system as claimed in claim 13, wherein said strobe and said SERS substrate are both located within a sampling head.

22. The system as claimed in claim 21, wherein the sampling head comprises a shroud.

23. The system as claimed in claim 22, wherein the shroud comprises a reflector, first strobe is positioned within reflector, the reflector having a parabolic shape in side profile, the parabolic shape described by an equation $x2 = 4py$, wherein p=at least one half of a diameter of a flash lamp portion of the first strobe.

24. The system as claimed in claim 13, further comprising at least one of a pump and a fan, said at least one pump and a fan for conveying an airborne sample containing the at least one liberated chemical over the SERS substrate.

25. The system as claimed in claim 24, where said at least one of a pump and a fan also thermally cools at least one of the strobe and the SERS substrate.

26. The system as claimed in claim 13, wherein said sampling head is operatively associated with at least one of a handle, a check-in counter, an X-ray machine, a conveyance mechanism, a floor, a sample container, a vehicle, a flap, a conveyor belt, a biasing member, and a hinged arm.

27. The system as claimed in claim 13, further comprising at least a second strobe located proximate said first strobe and co-directed at the target surface.

28. The system as claimed in claim 27, wherein the first and second strobes are operatively associated with a common shroud.

29. A system, comprising:
(a) a strobe operable to illuminate, with broadband radiation, a target surface to produce a sample;
(b) a SERS substrate operable to adsorb, from the sample, at least one chemical;
(c) a Raman excitation source for providing an excitation of the SERS substrate;
(d) a detector operable to detect the at least one chemical, the detector in operative communication with the SERS substrate;
wherein said SERS substrate and said Raman excitation source are spaced apart from the detector, wherein the detector is in a base unit, wherein said SERS substrate and said Raman excitation source are both located in a hand wand separate from the base unit, and wherein a fiber optic component carries Raman scattering from the SERS substrate to said detector.

30. The system as claimed in claim 29, wherein for the strobe imparts energy to a target surface, wherein said energy liberates the at least one chemical from the target surface and produces a sample for detection via Raman scattering.

31. The system as claimed in claim 30, further comprising a radiation source other than the strobe and Raman excitation source.

32. The system as claimed in claim 29, wherein the broadband radiation has a wavelength range of from about 300 nm to about 2 microns, wherein the strobe has a full light duration of up to about 3,000 μs, and wherein, during the full light duration, the strobe illuminates the target surface with radiation having an energy level of from about 0.4 to about 5 $J/cm^2$ of target surface.

33. The system as claimed in claim 31, wherein photons emitted from said radiation source clean at least a portion of said SERS substrate prior to the at least one chemical being adsorbed on to said SERS substrate.

34. The system as claimed in claim 31, wherein said radiation source, provides at least a pulse of photons for impinging and cleaning said SERS substrate.

35. A method for detecting a trace chemical by Raman spectroscopy, comprising:
illuminating, by a strobe and with broadband radiation, a target surface to produce a sample to be tested for a trace chemical, wherein the broadband radiation has a wavelength range of from about 300 nm to about 2 microns, wherein the strobe has a full light duration of up to about 3,000 μs, and wherein, during the full light duration, the strobe illuminates the target surface with a sufficient amount of radiation to vaporize a volatile substance and liberate at least some particles, the vaporized volatile substance and liberated particles being included in the sample;
transporting the sample to a SERS substrate located in close proximity to a port;
producing radiation, by a radiation source, wherein the port and radiation source are positioned in a first unit;
directing the radiation to the port;
contacting, on the SERS substrate, at least part of the sample with the radiation to produce scattered radiation;
optically focusing the scattered radiation onto a fiber optic component; and
transporting, by the fiber optic component, the scattered radiation to a detector for analysis, the detector being located in a second unit, wherein the first and second units are spatially dislocated and wherein the fiber optic component passes between the first and second units.

36. The method of claim 35, further comprising:
while the target surface is illuminated by the strobe, applying at least one of a positive and negative fluid pressure to the irradiated target surface to form the sample; and
collecting and transporting the sample to the port.

37. The method as claimed in claim 36, wherein the collecting step comprises the substep of providing at least one of a pump and a fan to pull the airborne sample to a SERS substrate before the analysis.

38. The method of claim 36, wherein the strobe and radiation source are located in a handheld unit, wherein the detector and power source are located in a discrete base unit, wherein a fiber optic component extends between the handheld unit and the base unit, wherein the handheld unit comprises a head containing the strobe and radiation source and a handgrip, and wherein the head is rotatable relative to the handgrip to adjust a position of the strobe relative to a surface to be sampled.

39. The method as claimed in claim 38, wherein the handheld unit includes the strobe and a SERS substrate for adsorbing the trace chemical and for conducting at least a portion of the surface enhanced Raman scattering.

40. A system for detecting a trace chemical by Raman spectroscopy, comprising:
   a strobe operable to illuminate a target surface with broadband radiation to produce a sample, wherein the broadband radiation has a wavelength range of from about 300 nm to about 2 microns, wherein the strobe has a full light duration of up to about 3,000 μs, and wherein, during the full light duration, the strobe illuminates the target surface with radiation having an energy level of from about 0.4 to about 5 J/cm$^2$ of target surface;
   an input to receive the sample, the sample to be tested for a trace chemical;
   a port to adsorb at least part of a sample for excitation to produce scattered radiation;
   a radiation source to produce the radiation, wherein the port and radiation source are positioned in a first unit;
   a detector, located in a second unit, to detect, using the scattered radiation, any trace chemical in the at least part of the sample, the detector being located in a second unit, wherein the first and second units are spatially dislocated;
   a fiber optic component to transport the scattered radiation to the detector for analysis, wherein the fiber optic component passes between the first and second units; and
   an optical system to direct the radiation to the port and focus the scattered radiation onto a fiber optic component.

41. The system of claim 40, further comprising:
   a positive and negative fluid pressure source positioned near the irradiated surface to collect produced particulates and vapor and form the sample fluid.

42. The system as claimed in claim 40, further comprising:
   at least one of a pump and a fan to pull the airborne sample to a SERS substrate before the analysis.

43. The system of claim 40, wherein the strobe and radiation source are located in a handheld unit, wherein the detector and power source are located in a discrete base unit, wherein a fiber optic component extends between the handheld unit and the base unit, wherein the handheld unit comprises a head containing the strobe and radiation source and a handgrip, and wherein the head is rotatable relative to the handgrip to adjust a position of the strobe relative to a surface to be sampled.

44. The system as claimed in claim 43, wherein the handheld unit includes the strobe and a SERS substrate for adsorbing the trace chemical and for conducting at least a portion of the surface enhanced Raman scattering.

45. The method of claim 1, wherein the pulsing step comprises the substeps:
   (A1) engaging, by a hinged arm, an item to be tested;
   (A2) rotating the hinged arm about an upper hinge;
   (A3) engaging, by a strobe device, the item;
   (A4) rotating, about a second hinge, the strobe device, comprising the strobe, to orient the strobe device to a sampling position relative to the item; and
   (A5) while the strobe device is in the sampling position, pulsing the strobe to illuminate the target surface on the item.

46. The method of claim 1, wherein the trace chemical in the sample is collected on a preconcentrator and further, comprising before the collecting step (b):
   desorbing the trace chemical from the preconcentrator to form the airborne sample.

47. The method of claim 1, wherein the pulsing step comprises the substeps:
   (A1) sensing an approaching item;
   (A2) at least one of raising and lowering a skid to contact the item, the skid comprising the strobe;
   (A3) sensing when the item is in a sampling position relative to the strobe;
   (A4) rotating, about a second hinge, the strobe device, comprising the strobe, to orient the strobe device to a sampling position relative to the item; and
   (A5) while the strobe device is in the sampling position, pulsing the strobe to illuminate the target surface on the item.

48. The method of claim 1, wherein the pulsing step comprises the substep:
   (A1) sensing an item of luggage in spatial proximity to the strobe; and
   (A2) pulsing the strobe to illuminate the target surface, the target surface being located on the luggage.

49. The method of claim 45, wherein the item is luggage.

50. The method of claim 47, wherein the item is luggage.

* * * * *